(12) United States Patent
Geall et al.

(10) Patent No.: US 9,254,265 B2
(45) Date of Patent: Feb. 9, 2016

(54) SMALL LIPOSOMES FOR DELIVERY OF IMMUNOGEN ENCODING RNA

(75) Inventors: Andrew Geall, Littleton, MA (US); Ayush Verma, Morrisville, NC (US)

(73) Assignee: NOVARTIS AG (CH)

( * ) Notice: Subject to any disclaimer, the term of this patent is extended or adjusted under 35 U.S.C. 154(b) by 0 days.

(21) Appl. No.: 13/819,245

(22) PCT Filed: Aug. 31, 2011

(86) PCT No.: PCT/US2011/049873
§ 371 (c)(1),
(2), (4) Date: Apr. 16, 2013

(87) PCT Pub. No.: WO2012/030901
PCT Pub. Date: Mar. 8, 2012

(65) Prior Publication Data
US 2013/0195969 A1  Aug. 1, 2013

Related U.S. Application Data

(60) Provisional application No. 61/378,831, filed on Aug. 31, 2010.

(51) Int. Cl.
*A61K 9/127* (2006.01)
*A61K 39/00* (2006.01)
*A61K 9/00* (2006.01)
*C12N 15/88* (2006.01)

(52) U.S. Cl.
CPC .............. *A61K 9/127* (2013.01); *A61K 9/0019* (2013.01); *A61K 9/1271* (2013.01); *A61K 9/1272* (2013.01); *A61K 39/00* (2013.01); *C12N 15/88* (2013.01); *A61K 9/1277* (2013.01); *A61K 2039/53* (2013.01); *A61K 2039/55555* (2013.01); *C12N 2710/16134* (2013.01); *C12N 2760/18534* (2013.01); *C12N 2770/36143* (2013.01); *C12N 2770/36171* (2013.01)

(58) Field of Classification Search
CPC ................ A61K 2039/53; A61K 2039/55555; A61K 9/127; A61K 9/0019
See application file for complete search history.

(56) References Cited

U.S. PATENT DOCUMENTS

| 5,013,556 | A | 5/1991 | Woodle et al. | |
|---|---|---|---|---|
| 5,279,833 | A | 1/1994 | Rose | |
| 5,750,390 | A | 5/1998 | Thompson et al. | |
| 5,972,704 | A | 10/1999 | Draper et al. | |
| 6,790,449 | B2 * | 9/2004 | Collins | 424/211.1 |
| 6,858,225 | B2 | 2/2005 | Semple et al. | |
| 6,890,554 | B2 | 5/2005 | Jessee et al. | |
| 7,250,404 | B2 | 7/2007 | Felgner et al. | |
| 7,303,881 | B2 | 12/2007 | Huang et al. | |
| 7,384,923 | B2 | 6/2008 | Gregoriadis | |
| 7,557,200 | B2 | 7/2009 | Wu | |
| 8,058,069 | B2 | 11/2011 | Yaworski et al. | |
| 8,877,206 | B2 | 11/2014 | Chen et al. | |
| 2003/0124134 | A1 * | 7/2003 | Edwards et al. | 424/184.1 |
| 2005/0042230 | A1 * | 2/2005 | Anderson et al. | 424/186.1 |
| 2006/0051405 | A1 * | 3/2006 | MacLachlan et al. | 424/450 |
| 2006/0063732 | A1 | 3/2006 | Vogel et al. | |
| 2006/0177819 | A1 * | 8/2006 | Smith et al. | 435/5 |
| 2009/0104226 | A1 | 4/2009 | Perri et al. | |
| 2010/0040650 | A1 * | 2/2010 | Crowe et al. | 424/212.1 |
| 2010/0173980 | A1 | 7/2010 | Valliant et al. | |
| 2011/0200667 | A1 | 8/2011 | Oñate Contreras | |
| 2012/0100207 | A1 * | 4/2012 | Motokui et al. | 424/450 |
| 2013/0171241 | A1 * | 7/2013 | Geall | 424/450 |
| 2013/0189351 | A1 * | 7/2013 | Geall | 424/450 |
| 2013/0195968 | A1 * | 8/2013 | Geall et al. | 424/450 |
| 2013/0202684 | A1 * | 8/2013 | Geall et al. | 424/450 |
| 2014/0141070 | A1 * | 5/2014 | Geall et al. | 424/450 |

FOREIGN PATENT DOCUMENTS

| CA | WO2005/120152 | * | 12/2005 | |
|---|---|---|---|---|
| EP | 0786522 | A2 | 7/1997 | |
| EP | 1637144 | A1 | 3/2006 | |
| JP | 2007-112768 | A1 | 5/2007 | |
| JP | WO/2011/001780 | * | 6/2011 | A61K 9/127 |
| WO | 99/52503 | A2 | 10/1999 | |
| WO | 03068190 | A1 | 8/2003 | |
| WO | 2005/120152 | A2 | 12/2005 | |
| WO | 2005/121348 | A1 | 12/2005 | |
| WO | WO 2007/047749 | | 4/2007 | |
| WO | 2008103276 | A2 | 8/2008 | |
| WO | 2008/137758 | A2 | 11/2008 | |
| WO | 2009/086558 | A1 | 7/2009 | |
| WO | 2009111088 | A2 | 7/2009 | |
| WO | 2010015098 | A1 | 2/2010 | |
| WO | 2011/005799 | A2 | 1/2011 | |
| WO | 2011008974 | A2 | 1/2011 | |

(Continued)

OTHER PUBLICATIONS

Lonez et al (Progress in Lipid Research. 2008; 47: 340-347).*

(Continued)

*Primary Examiner* — Scott Long

(74) *Attorney, Agent, or Firm* — Laurence A. Shumway; Helen Lee

(57) ABSTRACT

Nucleic acid immunization is achieved by delivering RNA encapsulated within a liposome. The RNA encodes an immunogen of interest, and the liposome has a diameter in the range of 60-180 nm, and ideally in the range 80-160 nm. Thus the invention provides a liposome having a lipid bilayer encapsulating an aqueous core, wherein: (i) the lipid bilayer has a diameter in the range of 60-180 nm; and (ii) the aqueous core includes a RNA which encodes an immunogen. These liposomes are suitable for in vivo delivery of the RNA to a vertebrate cell and so they are useful as components in pharmaceutical compositions for immunizing subjects against various diseases.

12 Claims, 20 Drawing Sheets

(56) References Cited

FOREIGN PATENT DOCUMENTS

| WO | 2011/076807 | A2 | 6/2011 |
|---|---|---|---|
| WO | 2012006378 | A2 | 1/2012 |
| WO | 2012031043 | A2 | 3/2012 |
| WO | 2012031046 | A1 | 3/2012 |
| WO | 2013033563 | A1 | 3/2013 |
| WO | 2005113782 | A1 | 9/2013 |

OTHER PUBLICATIONS

Fleeton et al (Journal of Infectious Diseases. 2001; 183:1395-1398).*
Ying et al. (Nature Medicine; Jul. 1999; 5(7): 823-827).*
Chiaramoni et al, "Liposome/DNA systems: correlation between hydrophobicity and DNA conformational changes", Journal of Biological Physics, 34(1-2), 179-88. (2008).
Chrai, et al, "Liposomes: A Review Part I: Manufacturing Issues", (April), Biotech Trends (2002).
Tseng et al., "Liposomes incorporated with cholesterol for drug release triggered by magnetic field", Journal of Medical and Biological Engineering, vol. 27, No. 1 29-34 (2007).
Ramana, et al, "Development of a liposomal nanodelivery system for nevirapine", Journal of Biomedical Science, 17, 57 (2010).
Samad et al, "Liposomal drug delivery systems: an updated review". Curr Drug Deliv. Oct. 2007;4(4):297-305 (2007).
Semple, et al., "Efficient encapsulation of antisense oligonucleotides in lipid vesicles using ionizable aminolipids: formation of novel small multilamellar vesicle structures", Biochimica et Biophysica Acta, 1510(1-2), 152-66,(2001).
Silva, et al, "Effect of ultrasound parameters for unilamellar liposome preparation", Ultrasonics Sonochemistry, 17(3), 628-32. doi:10.1016/j.ultsonch.2009.10.010 (2010).
Kulkarni, et al, "Factors affecting microencapsulation of drugs in liposomes", Journal of Microencapsulation, 12(3), 229-46. (1995).
Stuart, et al, "A new liposomal formulation for antisense oligodeoxynucleotides with small size, high incorporation efficiency and good stability", Biochimica et Biophysica Acta, 1463(2), 219-29 (2000).
Cannon, G., et al., "RNA Based Vaccines", DNA Cell Biol., 21(12): 953-961 (2002).
Caplen, N.J., "Nucleic acid transfer using cationic lipids", Methods in Mole. Biol., 133:1-19 (2000).
El Ouahabi, A. et al., "Double long-chain amidine liposome-mediated self replicating RNA transfection", FEBS Letters, 380(1-2): 108-112 (1996).
Elbashir et al., "Duplexes of 21-nucleotide RNAs mediate RNA interference in cultured mammalian cells" Nature, 411 (6836), 494-8 (2001).

Geall, A. et al "Nonviral delivery of self-amplifying RNA vaccines" Proceedings of the National Academy of Sciences of the United States of America, 109(36), 14604-9 (2012).
Gonçalves, et al. "The effect of liposome size on the final lipid/DNA ratio of cationic lipoplexes" Biophysical Journal, 86 (3), 1554-63 (2004).
Kita, H. et al. "Replication of Genetic Information with Self-Encoded Replicase in Liposomes" Chembiochem 9 (15) 2403-2410 (2008).
Levine, M., et al., "Vaccine development strategies for improving immunization: the role of modern immunology", Nature Immunol., 5(5): 460-464 (2004).
Martinon, F., et al., "Inductions of virus-specific cytotoxic T lymphocytes in vivo by liposome-entrapped mRNA", Eur. J. Immunol. 23: 1719-1722 (1993).
Mockey, M., et al., "mRNA-based cancer vaccine: prevention of B16 melanoma progression and metastasis by systemic injection of MART1 mRNA histidylated lipopolyplexes", Cancer Gene Therapy, 14(9): 802-814 (2007).
Saeki, Y., et al., "Development and Characterization of Cationic Liposomes Conjugated with HVJ (Sendai Virus): reciprocal Effect of Cationic Lipid for In Vitro and In Vivo Gene Transfer", Human gene Therapy, 8(17): 2134-2135 (1997).
Yamamoto, et al. (2009). Current prospects for mRNA gene delivery. Eur. J. of Pharma and Biopharm 71,484-489.
Zhang, J., et al., "Ionization Behavior of Amino Lipids for siRNA Delivery: Determinationof Ionization Constants, SAR, and the Impact of Lipid pKa on CationicLipid-Biomembrane Interactions," Langmuir: The ACS Journal of Surfaces and Colloids , ACS, vol. 15, No. 5, 1907-1914 (2011).
Zhou, W.Z., et al., "RNA Melanoma Vaccine: Induction of Antitumor Immunity by Human Glycoprotein 100 mRNA Immunization", Human Gene Therapy, 10(16): 2719-2724 (1999).
Geall, et al. "Using self-amplifying mRNA vaccines to facilitate a rapid response to pandemic influenza" Eur. Pharm. Review 19:3 20-23 (2014).
Hoerr et al. "In vivo application of RNA leads to induction of specific cytotoxic T lymphocytes and antibodies" Eur. J. Immunol. 30:1-7 (2000).
Leitner, et al. "DNA and RNA-based vaccines: principles, progress and prospects" Vaccine 18:765-77 (1999).
Vajdy, et al., "Mucosal adjuvants and delivery systems for protein-, DNA- and RNA-based vaccines." Immunol Cell Biol. Dec. 2004;82(6):617-27.
Vassilev, et al., Vassilev et al. "Microparticle-mediated RNA immunization against bovine viral diarrhea virus" Vaccine 19:2012-19 (2001).

* cited by examiner

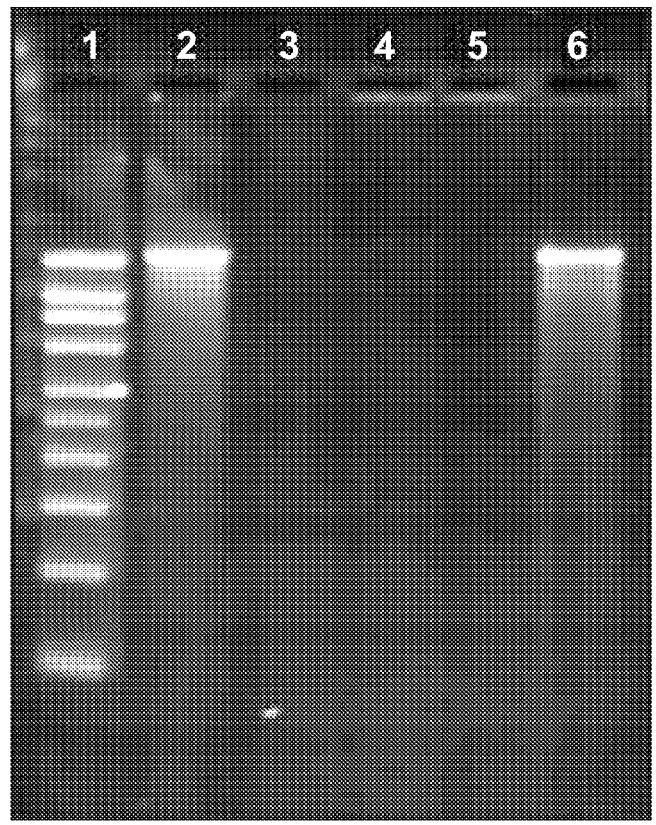
FIG. 1
FIG. 2
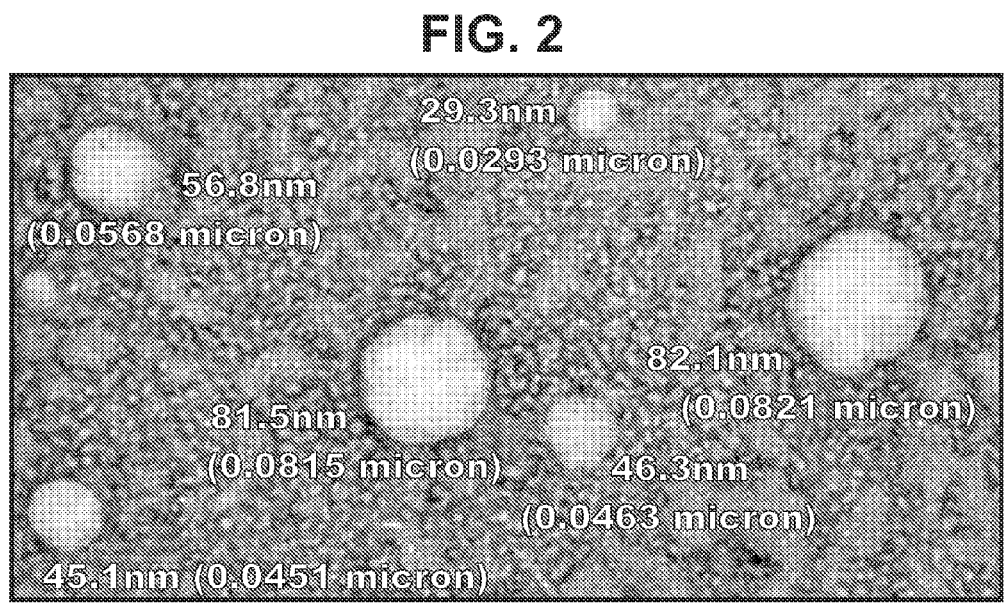

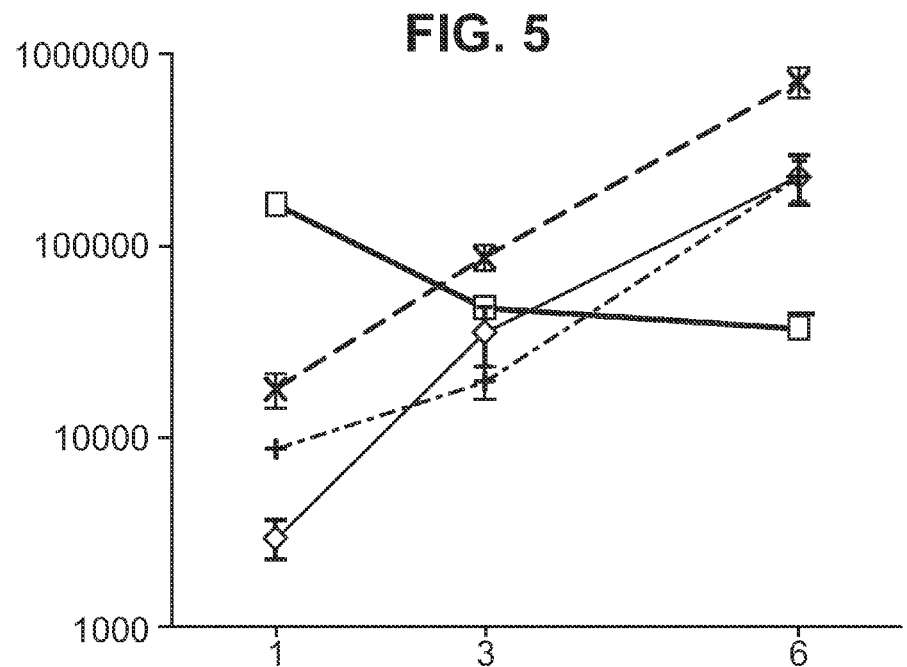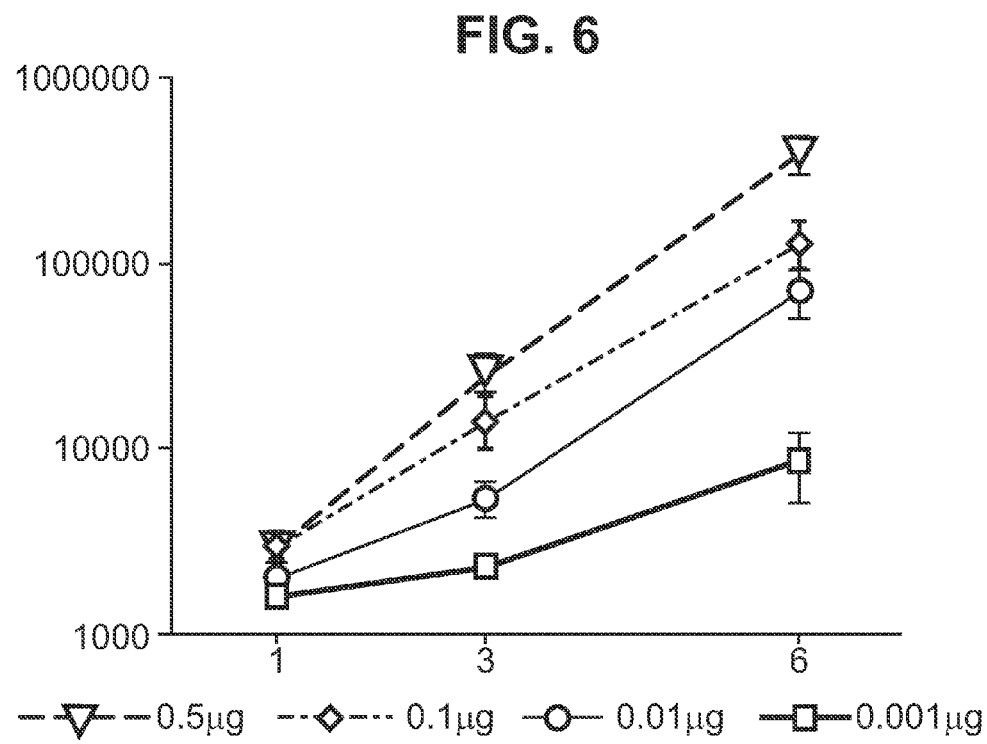

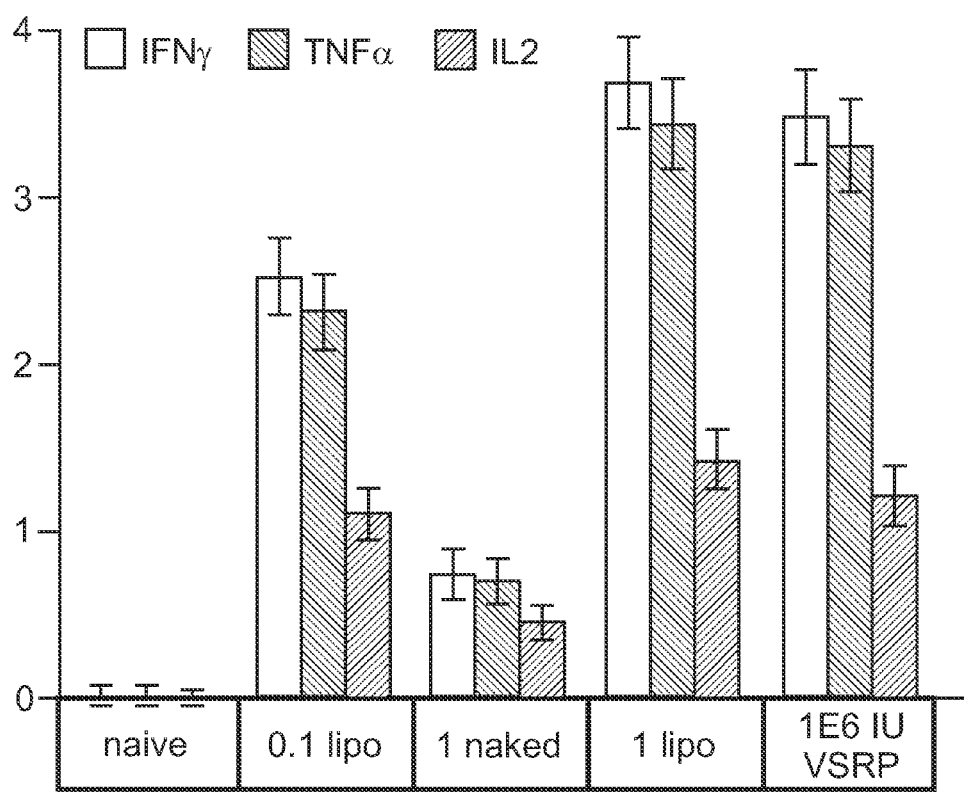
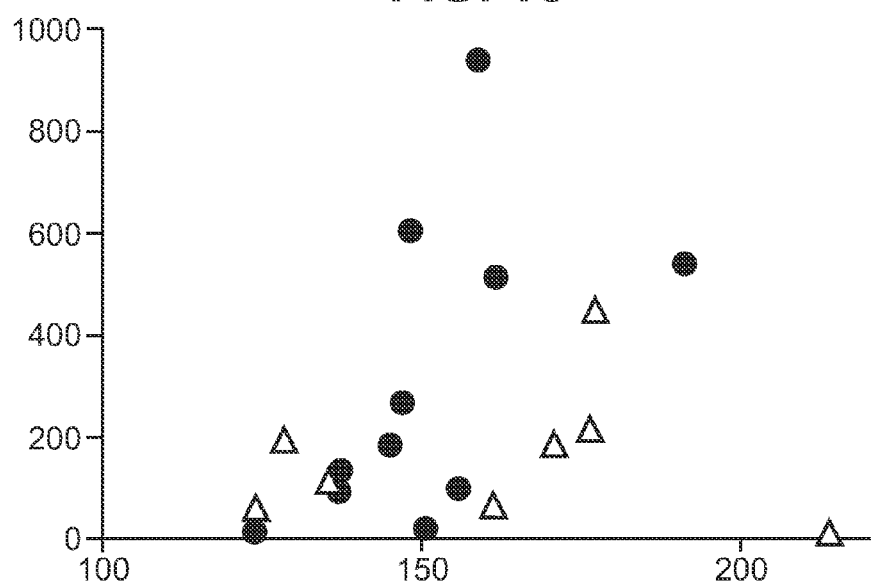

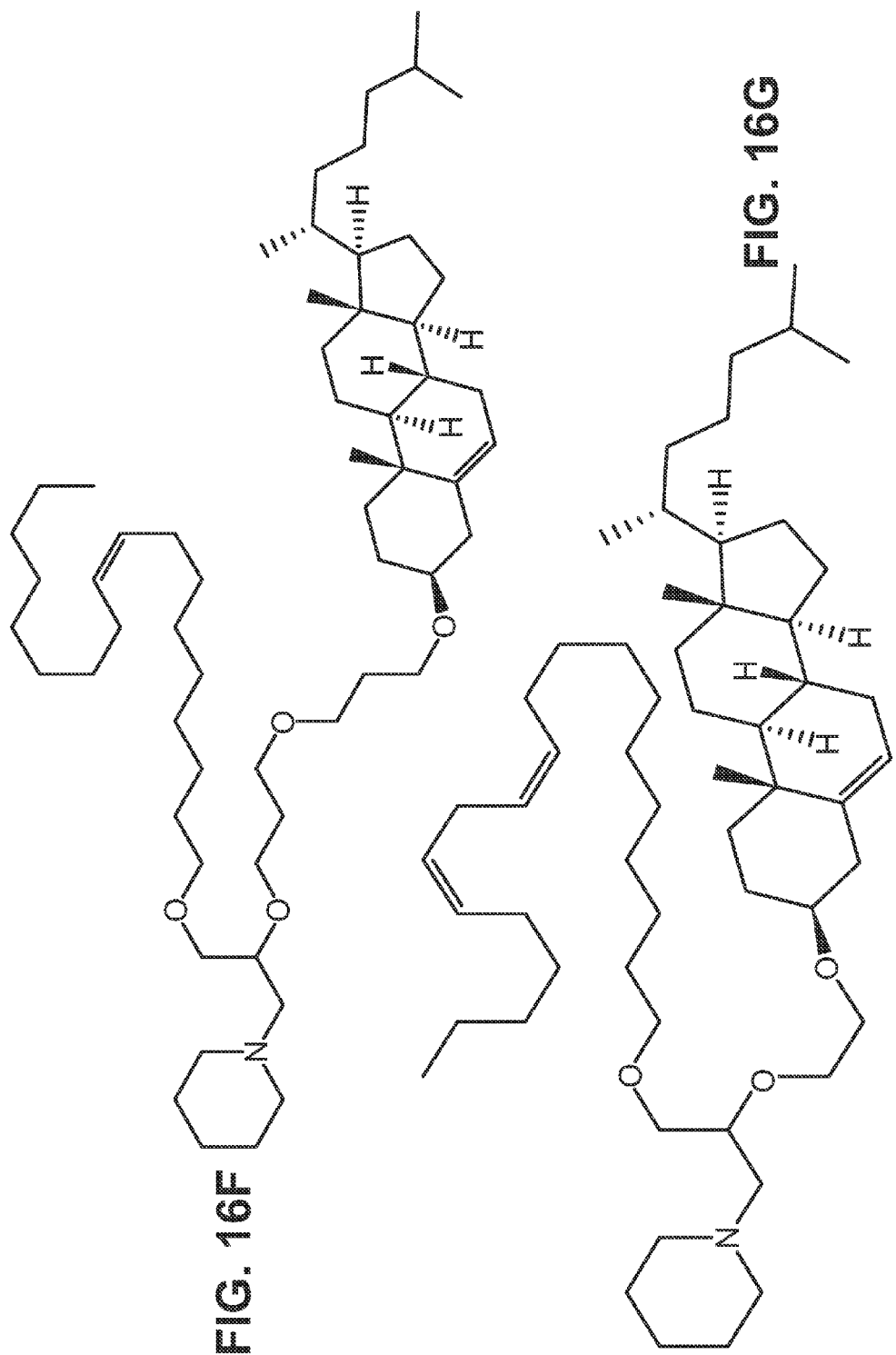

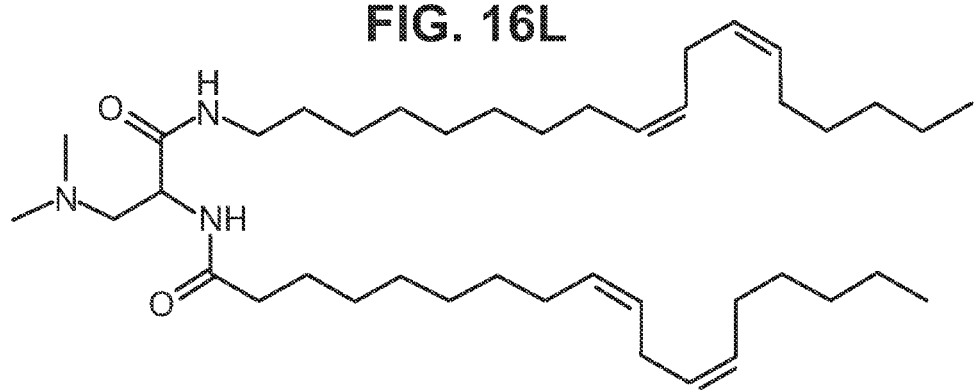
FIG. 16L
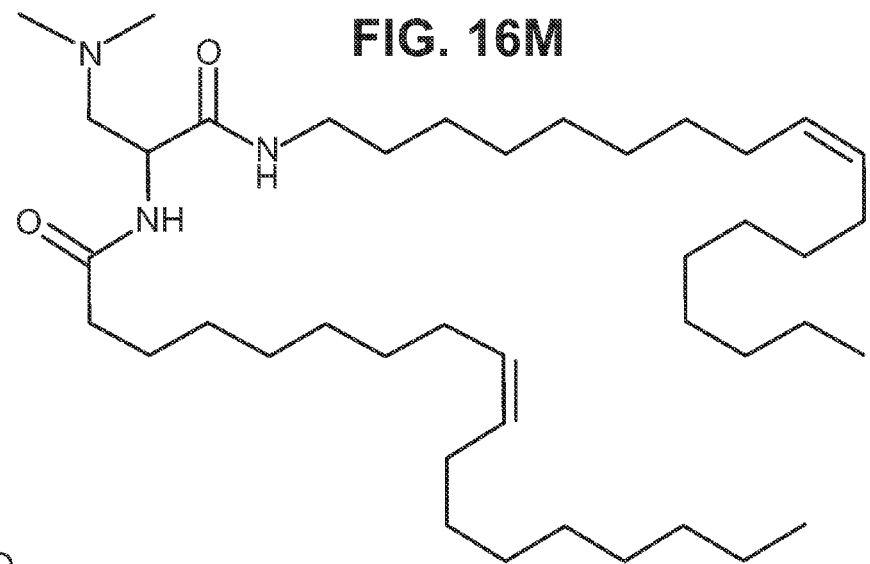
FIG. 16M
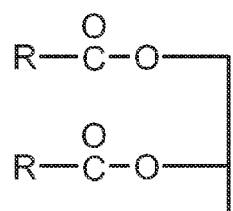
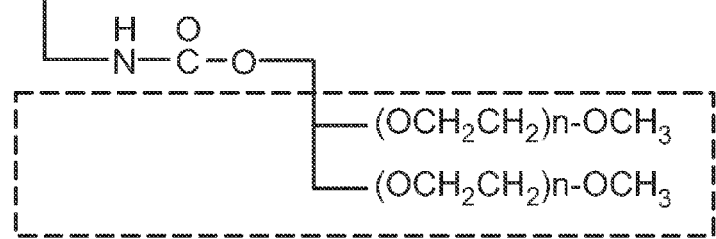
FIG. 17

SMALL LIPOSOMES FOR DELIVERY OF IMMUNOGEN ENCODING RNA

This application is the U.S. National Phase of International Application No. PCT/US2011/049873, filed Aug. 31, 2011 and published in English, which claims the benefit of U.S. Provisional Application No. 61/378,831, which was filed Aug. 31, 2010, the complete contents of which are hereby incorporated herein by reference for all purposes.

TECHNICAL FIELD

This invention is in the field of non-viral delivery of RNA for immunisation.

BACKGROUND ART

The delivery of nucleic acids for immunising animals has been a goal for several years. Various approaches have been tested, including the use of DNA or RNA, of viral or non-viral delivery vehicles (or even no delivery vehicle, in a "naked" vaccine), of replicating or non-replicating vectors, or of viral or non-viral vectors.

There remains a need for further and improved nucleic acid vaccines and, in particular, for improved ways of delivering nucleic acid vaccines.

DISCLOSURE OF THE INVENTION

According to the invention, nucleic acid immunisation is achieved by delivering RNA encapsulated within a liposome. The RNA encodes an immunogen of interest, and the liposome has a diameter in the range of 60-180 nm, and ideally in the range 80-160 nm. This size compares with, for example, a diameter of ~40 nm for an unenveloped alphavirus isometric protein capsid. The combination of efficient encapsulation of a RNA (particularly a self-replicating RNA) within a small liposome allows for efficient delivery to elicit a strong immune response.

Thus the invention provides a liposome within which RNA encoding an immunogen of interest is encapsulated, wherein the liposome has a diameter in the range of 60-180 nm. These liposomes are suitable for in vivo delivery of the RNA to a vertebrate cell and so they are useful as components in pharmaceutical compositions for immunising subjects against various diseases.

The invention also provides a process for preparing a RNA-containing liposome, comprising a step of mixing RNA with one or more lipids, under conditions such that the lipids form a liposome with a diameter in the range of 60-180 nm and in which the RNA is encapsulated.

The Liposome

The invention utilises liposomes within which immunogen-encoding RNA is encapsulated. Thus the RNA is (as in a natural virus) separated from any external medium. Encapsulation within the liposome has been found to protect RNA from RNase digestion. The liposomes can include some external RNA (e.g. on their surface), but at least half of the RNA (and ideally all of it) is encapsulated in the liposome's core. Encapsulation within liposomes is distinct from, for instance, the lipid/RNA complexes disclosed in reference 1, where RNA is mixed with pre-formed liposomes. Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic and others are cationic. Suitable classes of phospholipid include, but are not limited to, phosphatidylethanolamines, phosphatidylcholines, phosphatidylserines, and phosphatidyl-glycerols, and some useful phospholipids are listed in Table 1. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-di-O-octadecenyl-3-trimethylammonium propane (DOTMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC, DSPC, dodecylphosphocholine, 1,2-dioleoyl-sn-glycero-3-phosphatidylethanolamine (DOPE), and 1,2-di-phytanoyl-sn-glycero-3-phosphoethanolamine (DPyPE). The lipids can be saturated or unsaturated. The use of at least one unsaturated lipid for preparing liposomes is preferred. If an unsaturated lipid has two tails, both tails can be unsaturated, or it can have one saturated tail and one unsaturated tail. A lipid can include a steroid group in one tail e.g. as in RV05 (see also FIGS. 16A & C-K).

Thus, in some embodiments, the invention provides a liposome having a lipid bilayer encapsulating an aqueous core, wherein: (i) the liposome has a diameter in the range of 60-180 nm; and (ii) the aqueous core includes a RNA which encodes an immunogen.

Liposomes of the invention can be formed from a single lipid or from a mixture of lipids. A mixture may comprise (i) a mixture of anionic lipids (ii) a mixture of cationic lipids (iii) a mixture of zwitterionic lipids (iv) a mixture of anionic lipids and cationic lipids (v) a mixture of anionic lipids and zwitterionic lipids (vi) a mixture of zwitterionic lipids and cationic lipids or (vii) a mixture of anionic lipids, cationic lipids and zwitterionic lipids. Similarly, a mixture may comprise both saturated and unsaturated lipids. For example, a mixture may comprise DSPC (zwitterionic, saturated), DlinDMA (cationic, unsaturated), and/or DMG (anionic, saturated). Where a mixture of lipids is used, not all of the component lipids in the mixture need to be amphiphilic e.g. one or more amphiphilic lipids can be mixed with cholesterol.

Where a liposome of the invention is formed from a mixture of lipids, it is preferred that the proportion of those lipids which is cationic should be between 20-80% of the total amount of lipids e.g. between 30-70%, or between 40-60%. The remainder can be made of e.g. cholesterol (e.g. 35-50% cholesterol) and/or DMG (optionally PEGylated) and/or DSPC. Such mixtures are used below. These percentage values are mole percentages.

A liposome may include an amphiphilic lipid whose hydrophilic portion is PEGylated (i.e. modified by covalent attachment of a polyethylene glycol). This modification can increase stability and prevent non-specific adsorption of the liposomes. For instance, lipids can be conjugated to PEG using techniques such as those disclosed in reference 2 and 3. PEG provides the liposomes with a coat which can confer favourable pharmacokinetic characteristics. Various lengths of PEG can be used e.g. between 0.5-8 kDa.

Thus a liposome can be formed from a cationic lipid (e.g. DlinDMA, RV05), a zwitterionic lipid (e.g. DSPC, DPyPE), a cholesterol, and a PEGylated lipid. A mixture of DSPC, DlinDMA, PEG-DMG and cholesterol is used in the examples, as well as several further mixtures.

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter ≤50 nm, and LUVs have a diameter >50 nm. Liposomes of the invention are ideally LUVs with a diameter in the range of 60-180 nm, and preferably in the range of 80-160 nm. The liposomes preferably are substantially spherical. If they are not spherical, the term "diameter" refers to a liposome's largest cross-sectional diameter.

A liposome of the invention can be part of a composition comprising a plurality of liposomes, and the liposomes within the plurality can have a range of diameters. For a composition comprising a population of liposomes with different diameters: (i) at least 80% by number of the liposomes should have diameters in the range of 60-180 nm, and preferably in the range of 80-160 nm, and/or (ii) the average diameter (by intensity e.g. Z-average) of the population is ideally in the range of 60-180 nm, and preferably in the range of 80-160 nm.

Ideally, the distribution of liposome sizes (by intensity) has only one maximum i.e. there is a single population of liposomes distributed around an average (mode), rather than having two maxima. The diameters within a population of liposomes should ideally have a polydispersity index <0.2, and sometimes <0.1. The liposome/RNA complexes of reference 1 are expected to have a diameter in the range of 600-800 nm and to have a high polydispersity.

Apparatuses for determining the average particle diameter in a suspension of liposomes, and the size distribution, are commercially available. These typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvern Instruments (UK), or the Particle Size Distribution Analyzer instruments from Horiba (Kyoto, Japan). Dynamic light scattering is the preferred method by which liposome diameters are determined. For a population of liposomes, the preferred method for defining the average liposome diameter in a composition of the invention is a Z-average i.e. the intensity-weighted mean hydrodynamic size of the ensemble collection of liposomes measured by dynamic light scattering (DLS). The Z-average is derived from cumulants analysis of the measured correlation curve, wherein a single particle size (liposome diameter) is assumed and a single exponential fit is applied to the autocorrelation function. The cumulants analysis algorithm does not yield a distribution but, in addition to an intensity-weighted Z-average, gives a polydispersity index.

Techniques for preparing suitable liposomes are well known in the art e.g. see references 4 to 6. One useful method is described in reference 7 and involves mixing (i) an ethanolic solution of the lipids (ii) an aqueous solution of the nucleic acid and (iii) buffer, followed by mixing, equilibration, dilution and purification. Preferred liposomes of the invention are obtainable by this mixing process. To obtain liposomes with the desired diameter(s), mixing can be performed using a process in which two feed streams of aqueous RNA solution are combined in a single mixing zone with one stream of an ethanolic lipid solution, all at the same flow rate e.g. in a microfluidic channel as described below.

The RNA

Liposomes of the invention include a RNA molecule which (unlike siRNA) encodes an immunogen. After in vivo administration of the particles, RNA is released from the particles and is translated inside a cell to provide the immunogen in situ.

The RNA is +-stranded, and so it can be translated by cells without needing any intervening replication steps such as reverse transcription. It can also bind to TLR7 receptors expressed by immune cells, thereby initiating an adjuvant effect.

Preferred +-stranded RNAs are self-replicating. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall result of this sequence of transcriptions is a huge amplification in the number of the introduced replicon RNAs and so the encoded immunogen becomes a major polypeptide product of the cells.

One suitable system for achieving self-replication is to use an alphavirus-based RNA replicon. These +-stranded replicons are translated after delivery to a cell to give of a replicase (or replicase-transcriptase). The replicase is translated as a polyprotein which auto-cleaves to provide a replication complex which creates genomic −-strand copies of the +-strand delivered RNA. These −-strand transcripts can themselves be transcribed to give further copies of the +-stranded parent RNA and also to give a subgenomic transcript which encodes the immunogen. Translation of the subgenomic transcript thus leads to in situ expression of the immunogen by the infected cell. Suitable alphavirus replicons can use a replicase from a Sindbis virus, a Semliki forest virus, an eastern equine encephalitis virus, a Venezuelan equine encephalitis virus, etc. Mutant or wild-type viruses sequences can be used e.g. the attenuated TC83 mutant of VEEV has been used in replicons [8].

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non-structural replicase polyprotein, it is preferred that a self-replicating RNA molecule of the invention does not encode alphavirus structural proteins. Thus a preferred self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5') open reading frame encodes a replicase; the second (3') open reading frame encodes an immunogen. In some embodiments the RNA may have additional (e.g. downstream) open reading frames e.g. to encode further immunogens (see below) or to encode accessory polypeptides.

A self-replicating RNA molecule can have a 5' sequence which is compatible with the encoded replicase.

Self-replicating RNA molecules can have various lengths but they are typically 5000-25000 nucleotides long e.g. 8000-15000 nucleotides, or 9000-12000 nucleotides. Thus the RNA is longer than seen in siRNA delivery.

A RNA molecule useful with the invention may have a 5' cap (e.g. a 7-methylguanosine). This cap can enhance in vivo translation of the RNA.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding and thus promote adjuvant effects.

A RNA molecule may have a 3' poly-A tail. It may also include a poly-A polymerase recognition sequence (e.g. AAUAAA) near its 3' end.

A RNA molecule useful with the invention will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

A RNA molecule useful with the invention can conveniently be prepared by in vitro transcription (IVT). IVT can use a (cDNA) template created and propagated in plasmid form in bacteria, or created synthetically (for example by gene synthesis and/or polymerase chain-reaction engineering methods). For instance, a DNA-dependent RNA polymerase (such as the bacteriophage T7, T3 or SP6 RNA polymerases) can be used to transcribe the RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

As discussed in reference 9, the self-replicating RNA can include (in addition to any 5' cap structure) one or more nucleotides having a modified nucleobase. Thus the RNA can comprise m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2'-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6.-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-(carboxymethylaminomethyl-2-L-Omethyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); or ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, or an abasic nucleotide. For instance, a self-replicating RNA can include one or more modified pyrimidine nucleobases, such as pseudouridine and/or 5-methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7'-methylguanosine). In other embodiments, the RNA may include a 5' cap comprising a 7'-methylguanosine, and the first 1, 2 or 3 5' ribonucleotides may be methylated at the 2' position of the ribose.

A RNA used with the invention ideally includes only phosphodiester linkages between nucleosides, but in some embodiments it can contain phosphoramidate, phosphorothioate, and/or methylphosphonate linkages.

Ideally, a liposome includes fewer than 10 different species of RNA e.g. 5, 4, 3, or 2 different species; most preferably, a liposome includes a single RNA species i.e. all RNA molecules in the liposome have the same sequence and same length.

The amount of RNA per liposome can vary. The number of individual self-replicating RNA molecules per liposome is typically ≤50 e.g. <20, <10, <5, or 1-4 per liposome.

The Immunogen

RNA molecules used with the invention encode a polypeptide immunogen. After administration of the liposomes the RNA is translated in vivo and the immunogen can elicit an immune response in the recipient. The immunogen may elicit an immune response against a bacterium, a virus, a fungus or a parasite (or, in some embodiments, against an allergen; and in other embodiments, against a tumor antigen). The immune response may comprise an antibody response (usually including IgG) and/or a cell-mediated immune response. The polypeptide immunogen will typically elicit an immune response which recognises the corresponding bacterial, viral, fungal or parasite (or allergen or tumour) polypeptide, but in some embodiments the polypeptide may act as a mimotope to elicit an immune response which recognises a bacterial, viral, fungal or parasite saccharide. The immunogen will typically be a surface polypeptide e.g. an adhesin, a hemagglutinin, an envelope glycoprotein, a spike glycoprotein, etc.

The RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

Unlike references 1 and 10, the RNA encodes an immunogen. For the avoidance of doubt, the invention does not encompass RNA which encodes a firefly luciferase or which encodes a fusion protein of *E. coli* β-galactosidase or which encodes a green fluorescent protein (GFP). Such polypeptides may be useful as markers, or even in a gene therapy context, but the invention concerns delivery of RNA for eliciting an immunological response system. The optimum diameter of liposomes for gene therapy can differ from liposomes for immunisation purposes because target cells and tissues differ for these two approaches. Thus the immunogen also is not a self protein which is delivered to supplement or substitute for a defective host protein (as in gene therapy). Also, the RNA is not total mouse thymus RNA.

In some embodiments the immunogen elicits an immune response against one of these bacteria:

*Neisseria meningitidis*: useful immunogens include, but are not limited to, membrane proteins such as adhesins, autotransporters, toxins, iron acquisition proteins, and factor H binding protein. A combination of three useful polypeptides is disclosed in reference 11.

*Streptococcus pneumoniae*: useful polypeptide immunogens are disclosed in reference 12. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

*Streptococcus pyogenes*: useful immunogens include, but are not limited to, the polypeptides disclosed in references 13 and 14.

*Moraxella catarrhalis*.

*Bordetella pertussis*: Useful *pertussis* immunogens include, but are not limited to, *pertussis* toxin or toxoid (PT), filamentous haemagglutinin (FHA), pertactin, and agglutinogens 2 and 3.

*Staphylococcus aureus*: Useful immunogens include, but are not limited to, the polypeptides disclosed in reference 15, such as a hemolysin, esxA, esxB, ferrichrome-binding protein (sta006) and/or the sta011 lipoprotein.

*Clostridium tetani*: the typical immunogen is tetanus toxoid.

*Corynebacterium diphtheriae*: the typical immunogen is diphtheria toxoid.

*Haemophilus influenzae*: Useful immunogens include, but are not limited to, the polypeptides disclosed in references 16 and 17.

*Pseudomonas aeruginosa*

*Streptococcus agalactiae*: useful immunogens include, but are not limited to, the polypeptides disclosed in reference 13.

*Chlamydia trachomatis*: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in reference 18. LcrE [19] and HtrA [20] are two preferred immunogens.

*Chlamydia pneumoniae*: Useful immunogens include, but are not limited to, the polypeptides disclosed in reference 21.

*Helicobacter pylori*: Useful immunogens include, but are not limited to, CagA, VacA, NAP, and/or urease [22].

*Escherichia coli*: Useful immunogens include, but are not limited to, immunogens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC polypeptide immunogens are disclosed in references 23 and 24. Useful MNEC immunogens are disclosed in reference 25. A useful immunogen for several *E. coli* types is AcfD [26].

*Bacillus anthracis*

*Yersinia pestis*: Useful immunogens include, but are not limited to, those disclosed in references 27 and 28.

*Staphylococcus epidermis*

*Clostridium perfringens* or *Clostridium botulinums*

*Legionella pneumophila*

*Coxiella burnetii*

*Brucella*, such as *B. abortus, B. canis, B. melitensis, B. neotomae, B. ovis, B. suis, B. pinnipediae.*

*Francisella*, such as *F. novicida, F. philomiragia, F. tularensis.*

*Neisseria gonorrhoeae*

*Treponema pallidum*

*Haemophilus ducreyi*

*Enterococcus faecalis* or *Enterococcus faecium*

*Staphylococcus saprophyticus*
*Yersinia enterocolitica*
*Mycobacterium tuberculosis*
*Rickettsia*
*Listeria monocytogenes*
*Vibrio cholerae*
*Salmonella typhi*
*Borrelia burgdorferi*
*Porphyromonas gingivalis*
*Klebsiella*

In some embodiments the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: Viral immunogens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles virus).

Poxyiridae: Viral immunogens include, but are not limited to, those derived from Orthopoxvirus such as Variola vera, including but not limited to, Variola major and Variola minor.

Picornavirus: Viral immunogens include, but are not limited to, those derived from Picornaviruses, such as Enteroviruses, Rhinoviruses, Heparnavirus, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: Viral immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Heparnavirus: Viral immunogens include, but are not limited to, those derived from a Heparnavirus, such as hepatitis A virus (HAV).

Filovirus: Viral immunogens include, but are not limited to, those derived from a filovirus, such as an Ebola virus (including a Zaire, Ivory Coast, Reston or Sudan ebolavirus) or a Marburg virus.

Togavirus: Viral immunogens include, but are not limited to, those derived from a Togavirus, such as a Rubivirus, an Alphavirus, or an Arterivirus. This includes rubella virus.

Flavivirus: Viral immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: Viral immunogens include, but are not limited to, those derived from a Pestivirus, such as Bovine viral diarrhea (BVDV), Classical swine fever (CSFV) or Border disease (BDV).

Hepadnavirus: Viral immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: Viral immunogens include, but are not limited to, those derived from a Rhabdovirus, such as a Lyssavirus (e.g. a Rabies virus) and Vesiculovirus (VSV).

Caliciviridae: Viral immunogens include, but are not limited to, those derived from Calciviridae, such as Norwalk virus (Norovirus), and Norwalk-like Viruses, such as Hawaii Virus and Snow Mountain Virus.

Coronavirus: Viral immunogens include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Retrovirus: Viral immunogens include, but are not limited to, those derived from an Oncovirus, a Lentivirus (e.g. HIV-1 or HIV-2) or a Spumavirus.

Reovirus: Viral immunogens include, but are not limited to, those derived from an Orthoreovirus, a Rotavirus, an Orbivirus, or a Coltivirus.

Parvovirus: Viral immunogens include, but are not limited to, those derived from Parvovirus B19.

Herpesvirus: Viral immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: Viral immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: Viral immunogens include those derived from adenovirus serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album,* var. *discoides,* var. *ochraceum, Trichophyton violaceum,* and/or *Trichophyton faviforme;* or from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Can-* dida enolase, *Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In some embodiments the immunogen elicits an immune response against a parasite from the *Plasmodium* genus, such as *P. falciparum, P. vivax, P. malariae* or *P. ovale*. Thus the invention may be used for immunising against malaria. In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In some embodiments the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

Pharmaceutical Compositions

Liposomes of the invention are useful as components in pharmaceutical compositions for immunising subjects against various diseases. These compositions will typically include a pharmaceutically acceptable carrier in addition to the liposomes. A thorough discussion of pharmaceutically acceptable carriers is available in reference 29.

A pharmaceutical composition of the invention may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da. In some embodiments such agonist(s) are also encapsulated with the RNA inside liposomes, but in other embodiments they are unencapsulated.

Pharmaceutical compositions of the invention may include the liposomes in plain water (e.g. w.f.i.) or in a buffer e.g. a phosphate buffer, a Tris buffer, a borate buffer, a succinate buffer, a histidine buffer, or a citrate buffer. Buffer salts will typically be included in the 5-20 mM range.

Pharmaceutical compositions of the invention may have a pH between 5.0 and 9.5 e.g. between 6.0 and 8.0.

Compositions of the invention may include sodium salts (e.g. sodium chloride) to give tonicity. A concentration of 10±2 mg/ml NaCl is typical e.g. about 9 mg/ml.

Compositions of the invention may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 μM e.g. 0.1 mM. A citrate salt, such as sodium citrate, can also act as a chelator, while advantageously also providing buffering activity.

Pharmaceutical compositions of the invention may have an osmolality of between 200 mOsm/kg and 400 mOsm/kg, e.g. between 240-360 mOsm/kg, or between 290-310 mOsm/kg.

Pharmaceutical compositions of the invention may include one or more preservatives, such as thiomersal or 2-phenoxyethanol. Mercury-free compositions are preferred, and preservative-free vaccines can be prepared.

Pharmaceutical compositions of the invention are preferably sterile.

Pharmaceutical compositions of the invention are preferably non-pyrogenic e.g. containing <1 EU (endotoxin unit, a standard measure) per dose, and preferably <0.1 EU per dose.

Pharmaceutical compositions of the invention are preferably gluten free.

Pharmaceutical compositions of the invention may be prepared in unit dose form. In some embodiments a unit dose may have a volume of between 0.1-1.0 ml e.g. about 0.5 ml.

The compositions may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are typical.

Compositions comprise an immunologically effective amount of liposomes, as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The liposome and RNA content of compositions of the invention will generally be expressed in terms of the amount of RNA per dose. A preferred dose has ≤100 μg RNA (e.g. from 10-100 μg, such as about 10 μg, 25 μg, 50 μg, 75 μg or 100 μg), but expression can be seen at much lower levels e.g. ≤1 μg/dose, ≤100 ng/dose, ≤10 ng/dose, ≤1 ng/dose, etc The invention also provides a delivery device (e.g. syringe, nebuliser, sprayer, inhaler, dermal patch, etc.) containing a pharmaceutical composition of the invention. This device can be used to administer the composition to a vertebrate subject.

Liposomes of the invention do not contain ribosomes.

Methods of Treatment and Medical Uses

In contrast to the particles disclosed in reference 10, liposomes and pharmaceutical compositions of the invention are for in vivo use for eliciting an immune response against an immunogen of interest.

The invention provides a method for raising an immune response in a vertebrate comprising the step of administering an effective amount of a liposome or pharmaceutical composition of the invention. The immune response is preferably protective and preferably involves antibodies and/or cell-mediated immunity. The method may raise a booster response.

The invention also provides a liposome or pharmaceutical composition of the invention for use in a method for raising an immune response in a vertebrate.

The invention also provides the use of a liposome of the invention in the manufacture of a medicament for raising an immune response in a vertebrate.

By raising an immune response in the vertebrate by these uses and methods, the vertebrate can be protected against various diseases and/or infections e.g. against bacterial and/or viral diseases as discussed above. The liposomes and compositions are immunogenic, and are more preferably vaccine compositions. Vaccines according to the invention may either be prophylactic (i.e. to prevent infection) or therapeutic (i.e. to treat infection), but will typically be prophylactic.

The vertebrate is preferably a mammal, such as a human or a large veterinary mammal (e.g. horses, cattle, deer, goats, pigs). Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue; unlike reference 1, intraglossal injection is not typically used with the present invention). Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

The invention may be used to elicit systemic and/or mucosal immunity, preferably to elicit an enhanced systemic and/or mucosal immunity.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 30-36, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to charge, to cations, to anions, to zwitterions, etc., are taken at pH 7.

TLR3 is the Toll-like receptor 3. It is a single membrane-spanning receptor which plays a key role in the innate immune system. Known TLR3 agonists include poly(I:C). "TLR3" is the approved HGNC name for the gene encoding this receptor, and its unique HGNC ID is HGNC:11849. The RefSeq sequence for the human TLR3 gene is GI:2459625.

TLR7 is the Toll-like receptor 7. It is a single membrane-spanning receptor which plays a key role in the innate immune system. Known TLR7 agonists include e.g. imiquimod. "TLR7" is the approved HGNC name for the gene encoding this receptor, and its unique HGNC ID is HGNC:15631. The RefSeq sequence for the human TLR7 gene is GI:67944638.

TLR8 is the Toll-like receptor 8. It is a single membrane-spanning receptor which plays a key role in the innate immune system. Known TLR8 agonists include e.g. resiquimod. "TLR8" is the approved HGNC name for the gene encoding this receptor, and its unique HGNC ID is HGNC:15632. The RefSeq sequence for the human TLR8 gene is GI:20302165.

The RIG-I-like receptor ("RLR") family includes various RNA helicases which play key roles in the innate immune system [37]. RLR-1 (also known as RIG-I or retinoic acid inducible gene I) has two caspase recruitment domains near its N-terminus. The approved HGNC name for the gene encoding the RLR-1 helicase is "DDX58" (for DEAD (Asp-Glu-Ala-Asp) box polypeptide 58) and the unique HGNC ID is HGNC:19102. The RefSeq sequence for the human RLR-1 gene is GI:77732514. RLR-2 (also known as MDA5 or melanoma differentiation-associated gene 5) also has two caspase recruitment domains near its N-terminus. The approved HGNC name for the gene encoding the RLR-2 helicase is "IFIH1" (for interferon induced with helicase C domain 1) and the unique HGNC ID is HGNC:18873. The RefSeq sequence for the human RLR-2 gene is GI: 27886567. RLR-3 (also known as LGP2 or laboratory of genetics and physiology 2) has no caspase recruitment domains. The approved HGNC name for the gene encoding the RLR-3 helicase is "DHX58" (for DEXH (Asp-Glu-X-His) box polypeptide 58) and the unique HGNC ID is HGNC:29517. The RefSeq sequence for the human RLR-3 gene is GI:149408121.

PKR is a double-stranded RNA-dependent protein kinase. It plays a key role in the innate immune system. "EIF2AK2" (for eukaryotic translation initiation factor 2-alpha kinase 2) is the approved HGNC name for the gene encoding this enzyme, and its unique HGNC ID is HGNC:9437. The RefSeq sequence for the human PKR gene is GI:208431825.

BRIEF DESCRIPTION OF DRAWINGS

FIG. 1 shows a gel with stained RNA. Lanes show (1) markers (2) naked replicon (3) replicon after RNase treatment (4) replicon encapsulated in liposome (5) liposome after RNase treatment (6) liposome treated with RNase then subjected to phenol/chloroform extraction.

FIG. 2 is an electron micrograph of liposomes.

FIG. 5 shows protein expression at days 1, 3 and 6 after delivery of RNA as a virion-packaged replicon (squares), as naked RNA (diamonds), or in liposomes (+=0.1 µg, x=1 µg).

FIG. 6 shows protein expression at days 1, 3 and 6 after delivery of four different doses of liposome-encapsulated RNA.

FIG. 13 shows intracellular cytokine production after restimulation with synthetic peptides representing the major epitopes in the F protein, 4 weeks after a second dose. The y-axis shows the % cytokine+ of CD8+CD4−.

FIG. 15 shows anti-F titers expression (relative) two weeks after a first dose of replicon encoding F protein. The titers are plotted against liposome Z average diameter (nm).

FIGS. 16A to 16M show the structure of alternative cationic lipids: (A) RV05; (B) RV02; (C) RV04; (D) RV07; (E) RV03; (F) RV08; (G) RV09; (H) RV14; (I) RV10; (J) RV11; (K) RV15; (L) RV16; (M) RV17.

FIG. 17 shows the structure of a useful "split" PEG-conjugated lipid. The total molecular weight of PEG inside the box is 2000 in the tested liposomes.

MODES FOR CARRYING OUT THE INVENTION

RNA Replicons

Figure 3:
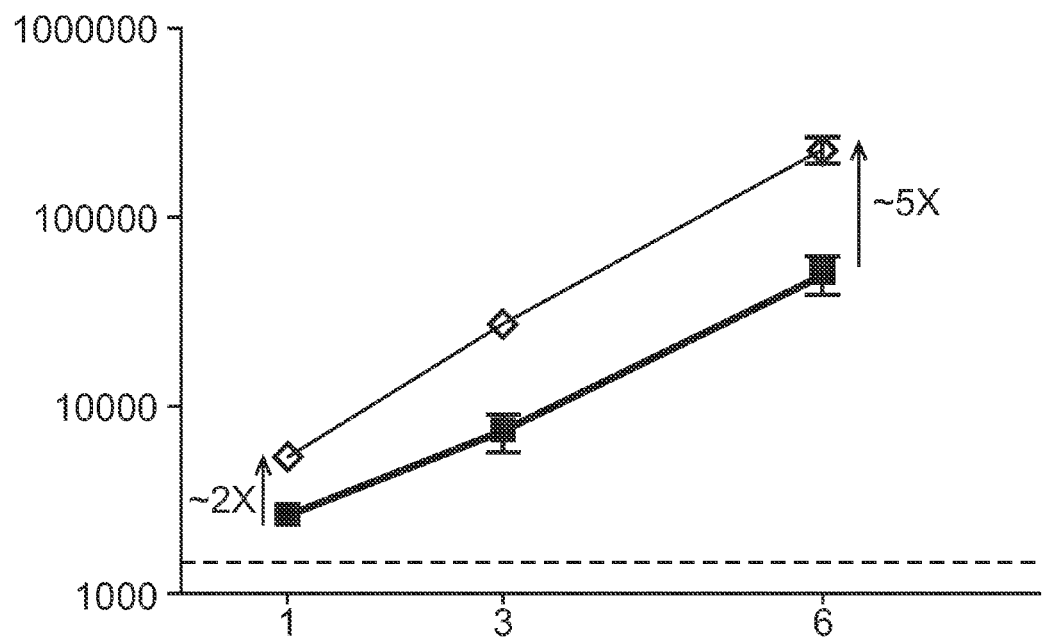
FIG. 3 shows protein expression (as relative light units, RLU) at days 1, 3 and 6 after delivery of RNA in large (lower line) or small (upper line) liposomes.

Various replicons are used below. In general these are based on a hybrid alphavirus genome with non-structural proteins from venezuelan equine encephalitis virus (VEEV), a packaging signal from VEEV, and a 3' UTR from Sindbis virus or a VEEV mutant. The replicon is about 10 kb long and has a poly-A tail.

Plasmid DNA encoding alphavirus replicons (named: pT7-mVEEV-FL.RSVF or A317; pT7-mVEEV-SEAP or A306; pSP6-VCR-GFP or A50) served as a template for synthesis of RNA in vitro. The replicons contain the alphavirus genetic elements required for RNA replication but lack those encoding gene products necessary for particle assembly; the structural proteins are instead replaced by a protein of interest (either a reporter, such as SEAP or GFP, or an immunogen, such as full-length RSV F protein) and so the replicons are incapable of inducing the generation of infectious particles. A bacteriophage (T7 or SP6) promoter upstream of the alphavirus cDNA facilitates the synthesis of the replicon RNA in vitro and a hepatitis delta virus (HDV) ribozyme immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) of each of the nucleoside triphosphates (ATP, CTP, GTP and UTP) following the instructions provided by the manufacturer (Ambion). Following transcription the template DNA was digested with TURBO DNase (Ambion). The replicon RNA was precipitated with LiCl and reconstituted in nuclease-free water. Uncapped RNA was capped post-transcriptionally with Vaccinia Capping Enzyme (VCE) using the ScriptCap m7G Capping System (Epicentre Biotechnologies) as outlined in the user manual; replicons capped in this way are given the "v" prefix e.g. vA317 is the A317 replicon capped by VCE. Post-transcriptionally capped RNA was precipitated with LiCl and reconstituted in nuclease-free water. The concentration of the RNA samples was determined by measuring $OD_{260nm}$. Integrity of the in vitro transcripts was confirmed by denaturing agarose gel electrophoresis.

Liposomal Encapsulation

RNA was encapsulated in liposomes made essentially by the method of references 7 and 38. The liposomes were made of 10% DSPC (zwitterionic), 40% DlinDMA (cationic), 48% cholesterol and 2% PEG-conjugated DMG (2 kDa PEG). These proportions refer to the % moles in the total liposome.

DlinDMA (1,2-dilinoleyloxy-N,N-dimethyl-3-aminopropane) was synthesized using the procedure of reference 2. DSPC (1,2-Diastearoyl-sn-glycero-3-phosphocholine) was purchased from Genzyme. Cholesterol was obtained from Sigma-Aldrich. PEG-conjugated DMG (1,2-dimyristoyl-sn-glycero-3-phosphoethanolamine-N-[methoxy(polyethylene glycol), ammonium salt), DOTAP (1,2-dioleoyl-3-trimethylammonium-propane, chloride salt) and DC-chol (3β-[N-(N', N'-dimethylaminoethane)-carbamoyl]cholesterol hydrochloride) were from Avanti Polar Lipids.

Briefly, lipids were dissolved in ethanol (2 ml), a RNA replicon was dissolved in buffer (2 ml, 100 mM sodium citrate, pH 6) and these were mixed with 2 ml of buffer followed by 1 hour of equilibration. The mixture was diluted with 6 ml buffer then filtered. The resulting product contained liposomes, with ~95% encapsulation efficiency.

For example, in one particular method, fresh lipid stock solutions were prepared in ethanol. 37 mg of DlinDMA, 11.8 mg of DSPC, 27.8 mg of cholesterol and 8.07 mg of PEG-DMG were weighed and dissolved in 7.55 mL of ethanol. The freshly prepared lipid stock solution was gently rocked at 37° C. for about 15 min to form a homogenous mixture. Then, 755 μL of the stock was added to 1.245 mL ethanol to make a working lipid stock solution of 2 mL. This amount of lipids was used to form liposomes with 250 μg RNA. A 2 mL working solution of RNA was also prepared from a stock solution of ~1 μg/μL in 100 mM citrate buffer (pH 6). Three 20 mL glass vials (with stir bars) were rinsed with RNase Away solution (Molecular BioProducts) and washed with plenty of MilliQ water before use to decontaminate the vials of RNases. One of the vials was used for the RNA working solution and the others for collecting the lipid and RNA mixes (as described later). The working lipid and RNA solutions were heated at 37° C. for 10 min before being loaded into 3 cc luer-lok syringes. 2 mL citrate buffer (pH 6) was loaded in another 3 cc syringe. Syringes containing RNA and the lipids were connected to a T mixer (PEEK™ 500 μm ID junction, Idex Health Science) using FEP tubing (fluorinated ethylene-propylene; all FEP tubing used had a 2 mm internal diameter and a 3 mm outer diameter; obtained from Idex Health Science). The outlet from the T mixer was also FEP tubing. The third syringe containing the citrate buffer was connected to a separate piece of tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 hour. 4 ml of the mixture was loaded into a 5 cc syringe, which was connected to a piece of FEP tubing and in another 5 cc syringe connected to an equal length of FEP tubing, an equal amount of 100 mM citrate buffer (pH 6) was loaded. The two syringes were driven at 7 mL/min flow rate using the syringe pump and the final mixture collected in a 20 mL glass vial (while stirring). Next, the mixture collected from the second mixing step (liposomes) were passed through a Mustang Q membrane (an anion-exchange support that binds and removes anionic molecules, obtained from Pall Corporation). Before using this membrane for the liposomes, 4 mL of 1 M NaOH, 4 mL of 1 M NaCl and 10 mL of 100 mM citrate buffer (pH 6) were successively passed through it. Liposomes were warmed for 10 min at 37° C. before passing through the membrane. Next, liposomes were concentrated to 2 mL and dialyzed against 10-15 volumes of 1X PBS using by tangential flow filtration before recovering the final product.

The TFF system and hollow fiber filtration membranes were purchased from Spectrum Labs (Rancho Dominguez) and were used according to the manufacturer's guidelines. Polysulfone hollow fiber filtration membranes with a 100 kD pore size cutoff and 8 cm² surface area were used. For in vitro and in vivo experiments formulations were diluted to the required RNA concentration with 1X PBS.

FIG. 2 shows an example electron micrograph of liposomes prepared by these methods. These liposomes contain encapsulated RNA encoding full-length RSV F antigen. Dynamic light scattering of one batch showed an average diameter of 141 nm (by intensity) or 78 nm (by number).

The percentage of encapsulated RNA and RNA concentration were determined by Quant-iT RiboGreen RNA reagent kit (Invitrogen), following manufacturer's instructions. The ribosomal RNA standard provided in the kit was used to generate a standard curve. Liposomes were diluted 10× or 100× in 1X TE buffer (from kit) before addition of the dye. Separately, liposomes were diluted 10× or 100× in 1X TE buffer containing 0.5% Triton X before addition of the dye (to disrupt the liposomes and thus to assay total RNA). Thereafter an equal amount of dye was added to each solution and then ~180 µL of each solution after dye addition was loaded in duplicate into a 96 well tissue culture plate. The fluorescence (Ex 485 nm, Em 528 nm) was read on a microplate reader. All liposome formulations were dosed in vivo based on the encapsulated amount of RNA.

Figure 4:
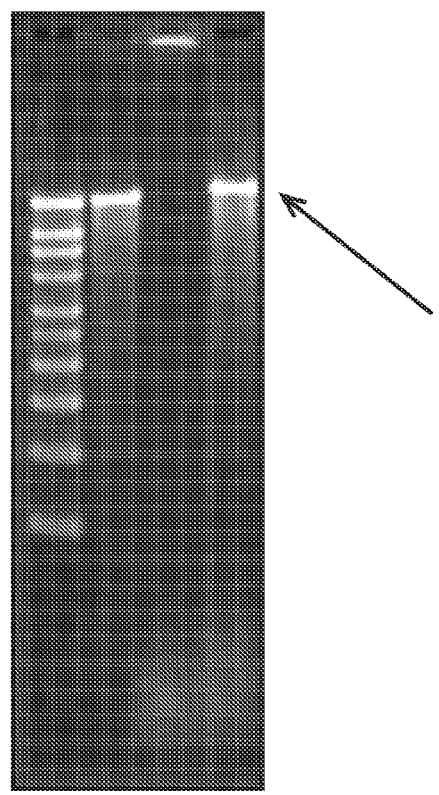
FIG. 4 shows a gel with stained RNA. Lanes show (1) markers (2) naked replicon (3) replicon encapsulated in liposome (4) liposome treated with RNase then subjected to phenol/chloroform extraction.

Encapsulation in liposomes was shown to protect RNA from RNase digestion. Experiments used 3.8 mAU of RNase A per microgram of RNA, incubated for 30 minutes at room temperature. RNase was inactivated with Proteinase K at 55° C. for 10 minutes. A 1:1 v/v mixture of sample to 25:24:1 v/v/v, phenol:chloroform:isoamyl alcohol was then added to extract the RNA from the lipids into the aqueous phase. Samples were mixed by vortexing for a few seconds and then placed on a centrifuge for 15 minutes at 12k RPM. The aqueous phase (containing the RNA) was removed and used to analyze the RNA. Prior to loading (400 ng RNA per well) all the samples were incubated with formaldehyde loading dye, denatured for 10 minutes at 65° C. and cooled to room temperature. Ambion Millennium markers were used to approximate the molecular weight of the RNA construct. The gel was run at 90 V. The gel was stained using 0.1% SYBR gold according to the manufacturer's guidelines in water by rocking at room temperature for 1 hour. FIG. 1 shows that RNase completely digests RNA in the absence of encapsulation (lane 3). RNA is undetectable after encapsulation (lane 4), and no change is seen if these liposomes are treated with RNase (lane 4). After RNase-treated liposomes are subjected to phenol extraction, undigested RNA is seen (lane 6). Even after 1 week at 4° C. the RNA could be seen without any fragmentation (FIG. 4, arrow). Protein expression in vivo was unchanged after 6 weeks at 4° C. and one freeze-thaw cycle. Thus liposome-encapsulated RNA is stable.

To assess in vivo expression of the RNA a reporter enzyme (SEAP; secreted alkaline phosphatase) was encoded in the replicon, rather than an immunogen. Expression levels were measured in sera diluted 1:4 in 1X Phospha-Light dilution buffer using a chemiluminescent alkaline phosphate substrate. 8-10 week old BALB/c mice (5/group) were injected intramuscularly on day 0, 50 µl per leg with 0.1 µg or 1 µg RNA dose. The same vector was also administered without the liposomes (in RNase free 1X PBS) at 1 µg. Virion-packaged replicons were also tested. Virion-packaged replicons used herein (referred to as "VRPs") were obtained by the methods of reference 39, where the alphavirus replicon is derived from the mutant VEEV or a chimera derived from the genome of VEEV engineered to contain the 3' UTR of Sindbis virus and a Sindbis virus packaging signal (PS), packaged by co-electroporating them into BHK cells with defective helper RNAs encoding the Sindbis virus capsid and glycoprotein genes.

As shown in FIG. 5, encapsulation increased SEAP levels by about ½ log at the 1 µg dose, and at day 6 expression from a 0.1 µg encapsulated dose matched levels seen with 1 µg unencapsulated dose. By day 3 expression levels exceeded those achieved with VRPs (squares). Thus expressed increased when the RNA was formulated in the liposomes relative to the naked RNA control, even at a 10× lower dose. Expression was also higher relative to the VRP control, but the kinetics of expression were very different (see FIG. 5). Delivery of the RNA with electroporation resulted in increased expression relative to the naked RNA control, but these levels were lower than with liposomes.

Figure 10:
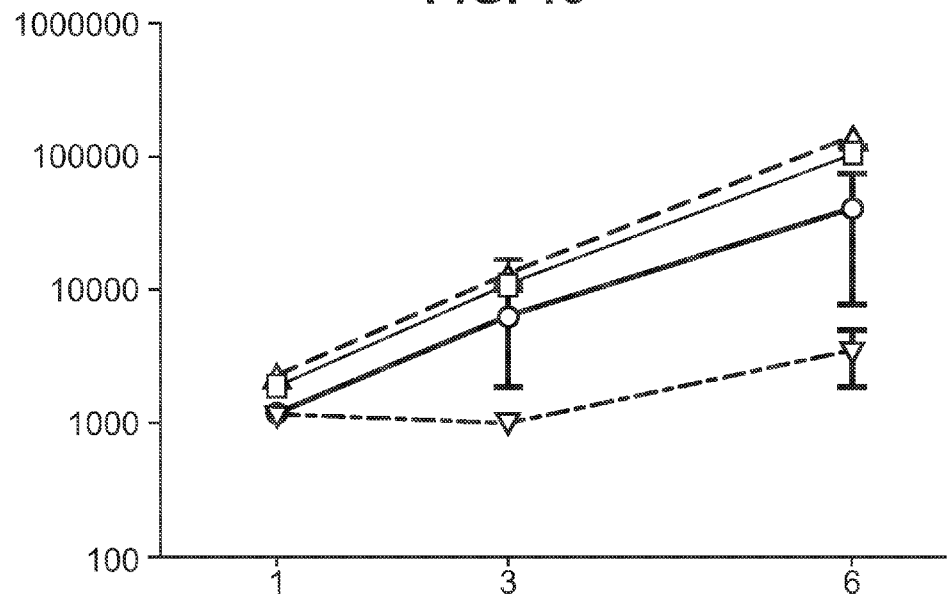
FIG. 10 shows expression levels after delivery of a replicon as naked RNA (circles), liposome-encapsulated RNA (triangle & square), or as a lipoplex (inverted triangle).

To assess whether the effect seen in the liposome groups was due merely to the liposome components, or was linked to the encapsulation, the replicon was administered in encapsulated form (with two different purification protocols, 0.1 µg RNA), or mixed with the liposomes after their formation (a non-encapsulated "lipoplex", 0.1 µg RNA), or as naked RNA (1 µg). FIG. 10 shows that the lipoplex gave the lowest levels of expression, showing that shows encapsulation is essential for potent expression.

Further SEAP experiments showed a clear dose response in vivo, with expression seen after delivery of as little as 1 ng RNA (FIG. 6). Further experiments comparing expression from encapsulated and naked replicons indicated that 0.01 µg encapsulated RNA was equivalent to 1 µg of naked RNA. At a 0.5 µg dose of RNA the encapsulated material gave a 12-fold higher expression at day 6; at a 0.1 µg dose levels were 24-fold higher at day 6.

Rather than looking at average levels in the group, individual animals were also studied. Whereas several animals were non-responders to naked replicons, encapsulation eliminated non-responders.

Further experiments replaced DlinDMA with DOTAP. Although the DOTAP liposomes gave better expression than naked replicon, they were inferior to the DlinDMA liposomes (2- to 3-fold difference at day 1).

Figure 7:
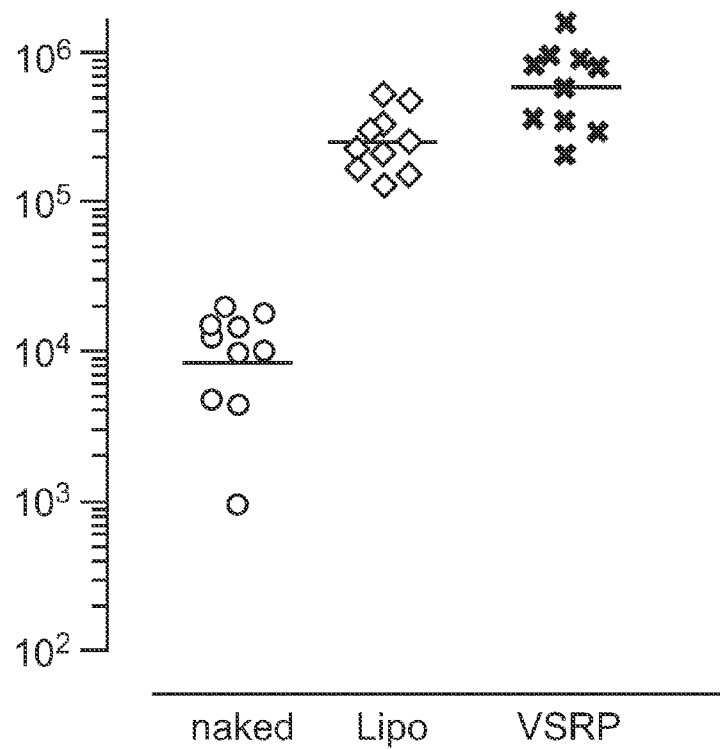
FIG. 7 shows anti-F IgG titers in animals receiving virion-packaged replicon (VRP or VSRP), 1 µg naked RNA, and 1 µg liposome-encapsulated RNA.
Figure 8:
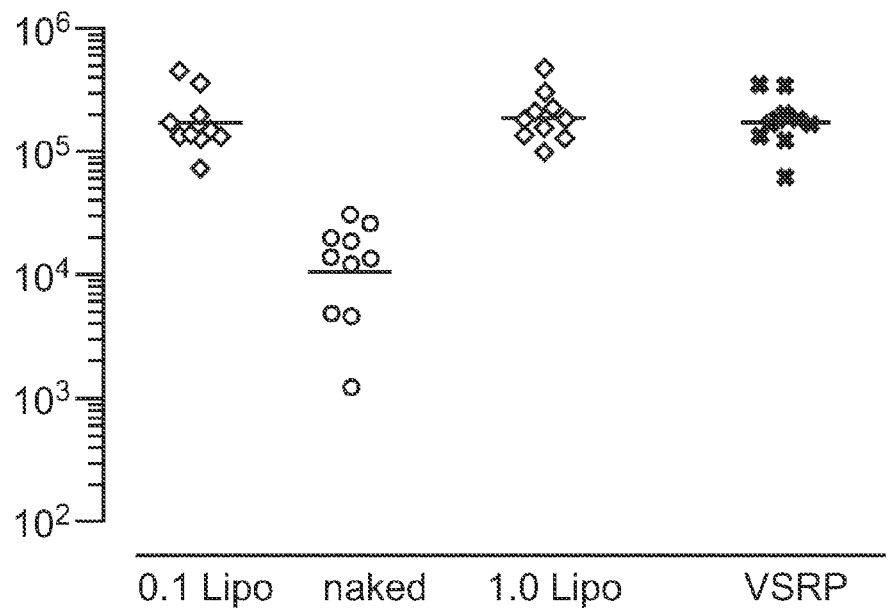
FIG. 8 shows anti-F IgG titers in animals receiving VRP, 1 µg naked RNA, and 0.1 g or 1 µg liposome-encapsulated RNA.
Figure 9:
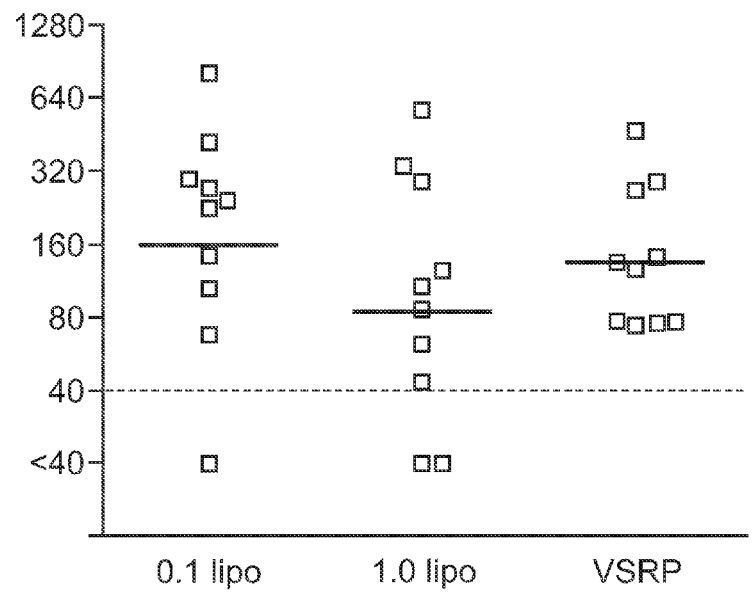
FIG. 9 shows neutralising antibody titers in animals receiving VRP or either 0.1 g or 1 µg liposome-encapsulated RNA.
Figure 12:
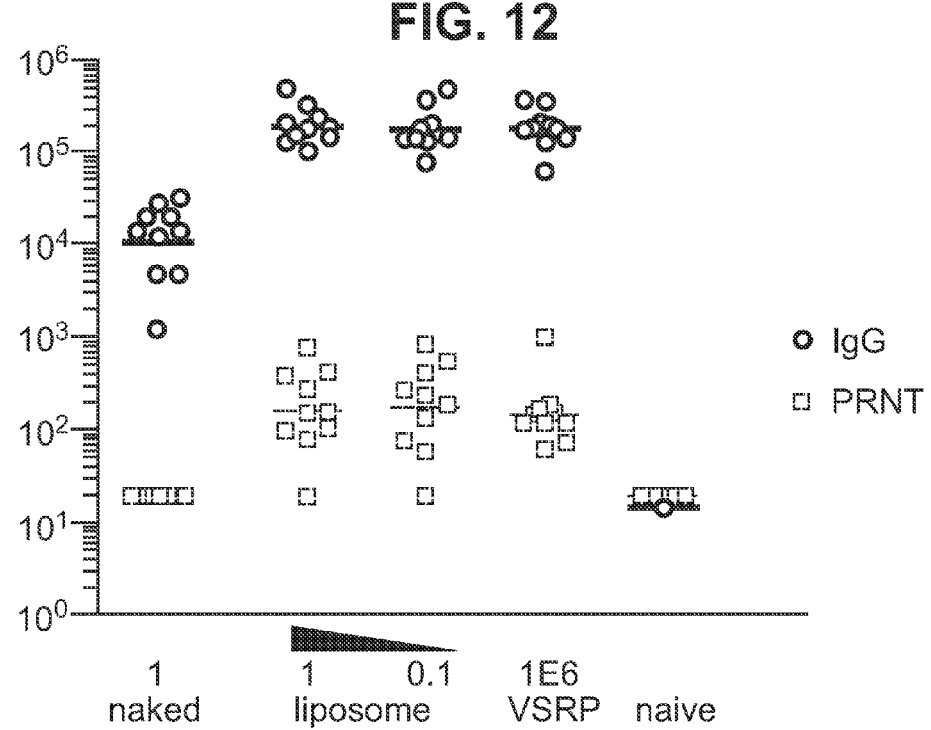
FIG. 12 shows F-specific IgG titers (circles) and PRNT titers (squares) after delivery of a replicon as naked RNA (1 µg), liposome-encapsulated RNA (0.1 or 1 µg), or packaged as a virion (VRP, $10^6$ IU). Titers in naïve mice are also shown. Solid lines show geometric means.

To assess in vivo immunogenicity a replicon was constructed to express full-length F protein from respiratory syncytial virus (RSV). This was delivered naked (1 µg), encapsulated in liposomes (0.1 or 1 µg), or packaged in virions (10⁶ IU; "VRP") at days 0 and 21. FIG. 7 shows anti-F IgG titers 2 weeks after the second dose, and the liposomes clearly enhance immunogenicity. FIG. 8 shows titers 2 weeks later, by which point there was no statistical difference between the encapsulated RNA at 0.1 µg, the encapsulated RNA at 1 µg, or the VRP group. Neutralisation titers (measured as 60% plaque reduction, "PRNT60") were not significantly different in these three groups 2 weeks after the second dose (FIG. 9). FIG. 12 shows both IgG and PRNT titers 4 weeks after the second dose.

FIG. 13 confirms that the RNA elicits a robust CD8 T cell response.

Further experiments compared F-specific IgG titers in mice receiving VRP, 0.1 µg liposome-encapsulated RNA, or 1 µg liposome-encapsulated RNA. Titer ratios (VRP: liposome) at various times after the second dose were as follows:

| | 2 weeks | 4 weeks | 8 weeks |
|---|---|---|---|
| 0.1 µg | 2.9 | 1.0 | 1.1 |
| 1 µg | 2.3 | 0.9 | 0.9 |

Thus the liposome-encapsulated RNA induces essentially the same magnitude of immune response as seen with virion delivery.

Figure 11:
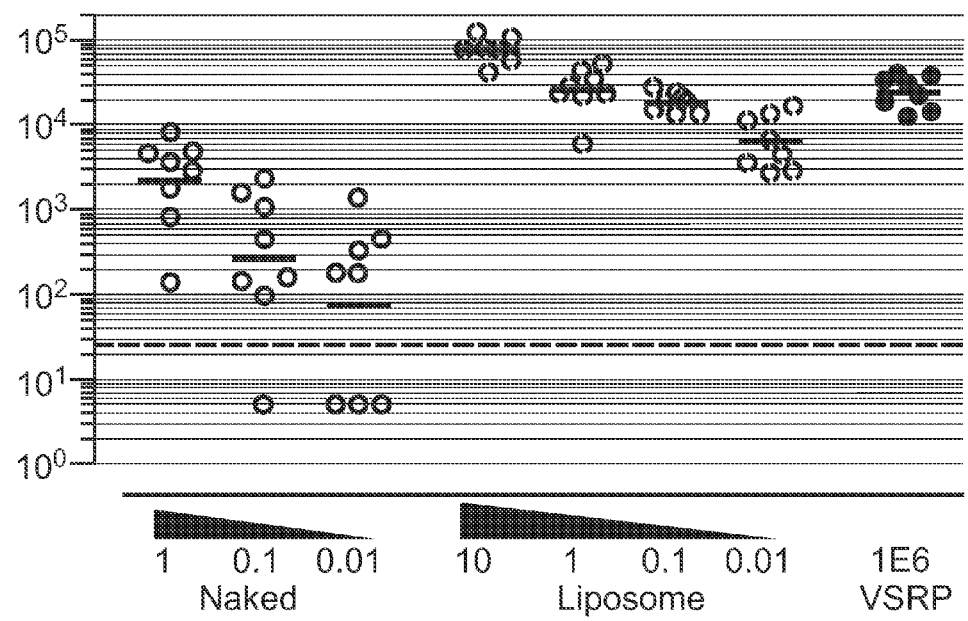
FIG. 11 shows F-specific IgG titers (2 weeks after second dose) after delivery of a replicon as naked RNA (0.01-1 µg), liposome-encapsulated RNA (0.01-10 µg), or packaged as a virion (VRP, $10^6$ infectious units or IU).

Further experiments showed superior F-specific IgG responses with a 10 µg dose, equivalent responses for 1 µg and 0.1 µg doses, and a lower response with a 0.01 µg dose. FIG. 11 shows IgG titers in mice receiving the replicon in naked form at 3 different doses, in liposomes at 4 different doses, or as VRP ($10^6$ IU). The response seen with 1 µg liposome-encapsulated RNA was statistically insignificant (ANOVA) when compared to VRP, but the higher response seen with 10 µg liposome-encapsulated RNA was statistically significant ($p<0.05$) when compared to both of these groups.

A further study confirmed that the 0.1 µg of liposome-encapsulated RNA gave much higher anti-F IgG responses (15 days post-second dose) than 0.1 µg of delivered DNA, and even was more immunogenic than 20 µg plasmid DNA encoding the F antigen, delivered by electroporation (Elgen™ DNA Delivery System, Inovio).

Cotton Rats

A study was performed in cotton rats (*Sigmodon hispidis*) instead of mice. At a 1 µg dose liposome encapsulation increased F-specific IgG titers by 8.3-fold compared to naked RNA and increased PRNT titers by 9.5-fold. The magnitude of the antibody response was equivalent to that induced by $5\times10^6$ IU VRP. Both naked and liposome-encapsulated RNA were able to protect the cotton rats from RSV challenge ($1\times10^5$ plaque forming units), reducing lung viral load by at least 3.5 logs. Encapsulation increased the reduction by about 2-fold.

Further work in cotton rats used four different replicons: vA317 expresses full-length RSV-F; vA318 expresses truncated (transmembrane and cytoplasmic tail removed) RSV-F; vA142 expresses RSV-F with its fusion peptide deleted; vA140 expresses the truncated RSV-F also without its peptide. Cotton rats, 4 to 8 animals per group, were given intramuscular vaccinations (100 µL in one leg) on days 0 and 21 with the four different replicons at two doses (1.0 and 0.1 µg) formulated in liposomes made using 2 kDa PEG-conjugated DMG by method (D), but with a 150 µg RNA batch size. Control groups received a RSV-F subunit protein vaccine (5 µg) adjuvanted with alum (8 animals/group), VRPs expressing full-length RSV-F ($1\times10^6$ IU, 8 animals/group), or naïve control (4 animals/group). Serum was collected for antibody analysis on days 0, 21 and 34.

F-specific serum IgG titers and RSV serum neutralizing antibody titers on day 21 and 34 were:

| Group | IgG, day 21 | IgG, day 34 | NT, day 21 | NT, day 34 |
|---|---|---|---|---|
| 1 µg vA317 | 915 | 2249 | 115 | 459 |
| 0.1 µg vA317 | 343 | 734 | 87 | 95 |
| 1 µg vA318 | 335 | 1861 | 50 | 277 |
| 0.1 µg vA318 | 129 | 926 | 66 | 239 |
| 1 µg vA142 | 778 | 4819 | 92 | 211 |
| 0.1 µg vA142 | 554 | 2549 | 78 | 141 |
| 1 µg vA140 | 182 | 919 | 96 | 194 |
| 0.1 µg vA140 | 61 | 332 | 29 | 72 |
| 5 µg F timer subunit/alum | 13765 | 86506 | 930 | 4744 |
| $1\times10^6$ IU VRP-F full | 1877 | 19179 | 104 | 4528 |
| Naïve | 5 | 5 | 10 | 15 |

All four replicons evaluated in this study (vA317, vA318, vA142, vA140) were immunogenic in cotton rats when delivered by liposome, although serum neutralization titers were at least ten-fold lower than those induced by adjuvanted protein vaccines or by VRPs. The liposome/RNA vaccines elicited serum F-specific IgG and RSV neutralizing antibodies after the first vaccination, and a second vaccination boosted the response effectively. F-specific IgG titers after the second vaccination with 1 µg replicon were 2- to 3-fold higher than after the second vaccination with 0.1 µg replicon. The four replicons elicited comparable antibody titers, suggesting that full length and truncated RSV-F, each with or without the fusion peptide, are similarly immunogenic in cotton rats.

Further work in cotton rats again used the vA317, vA318 and vA142 replicons. Cotton rats, 2-8 animals per group, were given intramuscular vaccinations (100 µL in one leg) on days 0 and 21 with the replicons (0.1 or 1 µg) encapsulated in RV01 liposomes (with PEG-2000) made by method (D) but with a 150 µg RNA batch size. Control groups received the RSV-F subunit protein vaccine (5 µg) adjuvanted with alum or VRPs expressing full-length RSV-F ($1\times10^6$ IU, 8 animals/group). All these animals received a third vaccination (day 56) with RSV-F subunit protein vaccine (5 µg) adjuvanted with alum. In addition there was a naïve control (4 animals/group). In addition, an extra group was given bilateral intramuscular vaccinations (50 µL per leg) on days 0 and 56 with 1 µg vA317 RNA in liposomes but did not receive a third vaccination with the subunit protein vaccine.

Serum was collected for antibody analysis on days 0, 21, 35, 56, 70, plus days 14, 28 & 42 for the extra group. F-specific serum IgG titers (GMT) were as follows:

| | Day 21 | Day 35 | Day 56 | Day 70 |
|---|---|---|---|---|
| 1 µg vA318 | 260 | 1027 | 332 | 14263 |
| 0.1 µg vA318 | 95 | 274 | 144 | 2017 |
| 1 µg vA142 | 483 | 1847 | 1124 | 11168 |
| 0.1 µg vA142 | 314 | 871 | 418 | 11023 |
| 1 µg vA317 | 841 | 4032 | 1452 | 13852 |
| $1\times10^6$ VRP (F-full) | 2075 | 3938 | 1596 | 14574 |
| 5 µg F trimer subunit/alum | 12685 | 54526 | 25846 | 48864 |
| Naïve | 5 | 5 | 5 | 5 |

Serum neutralisation titers were as follows (60% RSV neutralization titers for 2 pools of 3-4 animals per group, GMT of these 2 pools per group):

| | Day 21 | Day 35 | Day 56 | Day 70 |
|---|---|---|---|---|
| 1 µg vA318 | 58 | 134 | 111 | 6344 |
| 0.1 µg vA318 | 41 | 102 | 63 | 6647 |
| 1 µg vA142 | 77 | 340 | 202 | 5427 |
| 0.1 µg vA142 | 35 | 65 | 56 | 2223 |
| 1 µg vA317 | 19 | 290 | 200 | 4189 |
| $1\times10^6$ VRP (F-full) | 104 | 1539 | 558 | 2876 |
| 5 µg F trimer subunit/alum | 448 | 4457 | 1630 | 3631 |
| Naïve | 10 | 10 | 10 | |

Serum titers and neutralising titers for the extra group were as follows:

|     | Day |     |     |     |     |     |     |
| --- | --- | --- | --- | --- | --- | --- | --- |
|     | 14  | 21  | 28  | 35  | 42  | 56  | 70  |
| IgG | 397 | 561 | 535 | 501 | 405 | 295 | 3589 |
| NT  | 52  | 82  | 90  | 106 | 80  | 101 | 1348 |

Thus the replicons are confirmed as immunogenic in cotton rats, eliciting serum F-specific IgG and RSV neutralizing antibodies after the first vaccination. A second vaccination boosted the responses effectively. F-specific IgG titers after the second vaccination with 1.0 μg replicon were 1.5 to 4-fold higher than after the second vaccination with 0.1 μg replicon.

The third vaccination (protein at day 56) did not boost titers in cotton rats previously vaccinated with F trimer subunit+ alum, but it did provide a large boost to titers in cotton rats previously vaccinated with replicon. In most cases the RSV serum neutralization titers after two replicon vaccinations followed by protein boost were equal to or greater than titers induced by two or three sequential protein vaccinations.

This study also evaluated the kinetics of the antibody response to 1.0 μg vA317. F-specific serum IgG and RSV neutralization titers induced by a single vaccination reached their peak around day 21 and were maintained through at least day 56 (50-70% drop in F-specific IgG titer, little change in RSV neutralization titer). A homologous second vaccination was given to these animals on day 56, and boosted antibody titers to a level at least equal to that achieved when the second vaccination was administered on day 21.

Further experiments involved a viral challenge. The vA368 replicon encodes the full-length wild type surface fusion glycoprotein of RSV with the fusion peptide deleted, with expression driven by the EV71 IRES. Cotton rats, 7 per group, were given intramuscular vaccinations (100 μL per leg) on days 0 and 21 with vA368 in liposomes prepared by method (H), 175 μg RNA batch size, or with VRPs having the same replicon. The liposomes included 2 kDa PEG, conjugated to DMG. A control group received 5 μg alum-adjuvanted protein, and a naïve control group was also included.

All groups received an intranasal challenge (i.n.) with 1×10$^6$ PFU RSV four weeks after the final immunization. Serum was collected for antibody analysis on days 0, 21, 35. Viral lung titers were measured 5 days post challenge. Results were as follows:

|        | Liposome | VRP  | Protein | Naïve |
| ------ | -------- | ---- | ------- | ----- |
| F-specific Serum IgG titers (GMT) | | | | |
| Day 21 | 370      | 1017 | 28988   | 5     |
| Day 35 | 2636     | 2002 | 113843  | 5     |
| Neutralising titers (GMT) | | | | |
| Day 21 | 47       | 65   | 336     | 10    |
| Day 35 | 308      | 271  | 5188    | 10    |
| Lung viral load (pfu per gram of lung) | | | | |
| Day 54 | 422      | 225  | 124     | 694110 |

Thus the RNA vaccine reduced the lung viral load by over three logs, from approximately $10^6$ PFU/g in unvaccinated control cotton rats to less than $10^3$ PFU/g in vaccinated cotton rats.

Large Mammal Study

A large-animal study was performed in cattle. Calves (4-6 weeks old, ~60-80 kg, 5 per group) were immunised with 66 μg of replicon vA317 encoding full-length RSV F protein at days 0, 21, 86 and 146. The replicons were formulated inside liposomes made by method (E) but with a 1.5 mg RNA batch size; they had 40% DlinDMA, 10% DSPC, 48% cholesterol, and 2% PEG-2000 conjugated to DMG. PBS alone was used as a negative control, and a licensed vaccine was used as a positive control ("Triangle 4" from Fort Dodge, containing killed virus). All calves received 15 μg F protein adjuvanted with the MF59 emulsion on day 146.

The RNA vaccines encoded human RSV F whereas the "Triangle 4" vaccine contains bovine RSV F, but the RSV F protein is highly conserved between BRSV and HRSV.

Calves received 2 ml of each experimental vaccine, administered intramuscularly as 2×1 ml on each side of the neck. In contrast, the "Triangle 4" vaccine was given as a single 2 ml dose in the neck.

Serum was collected for antibody analysis on days 0, 14, 21, 35, 42, 56, 63, 86, 100, 107, 114, 121, 128, 135, 146, 160, 167, 174, 181, 188, 195, and 202. If an individual animal had a titer below the limit of detection it was assigned a titer of 5.

Figure 14:
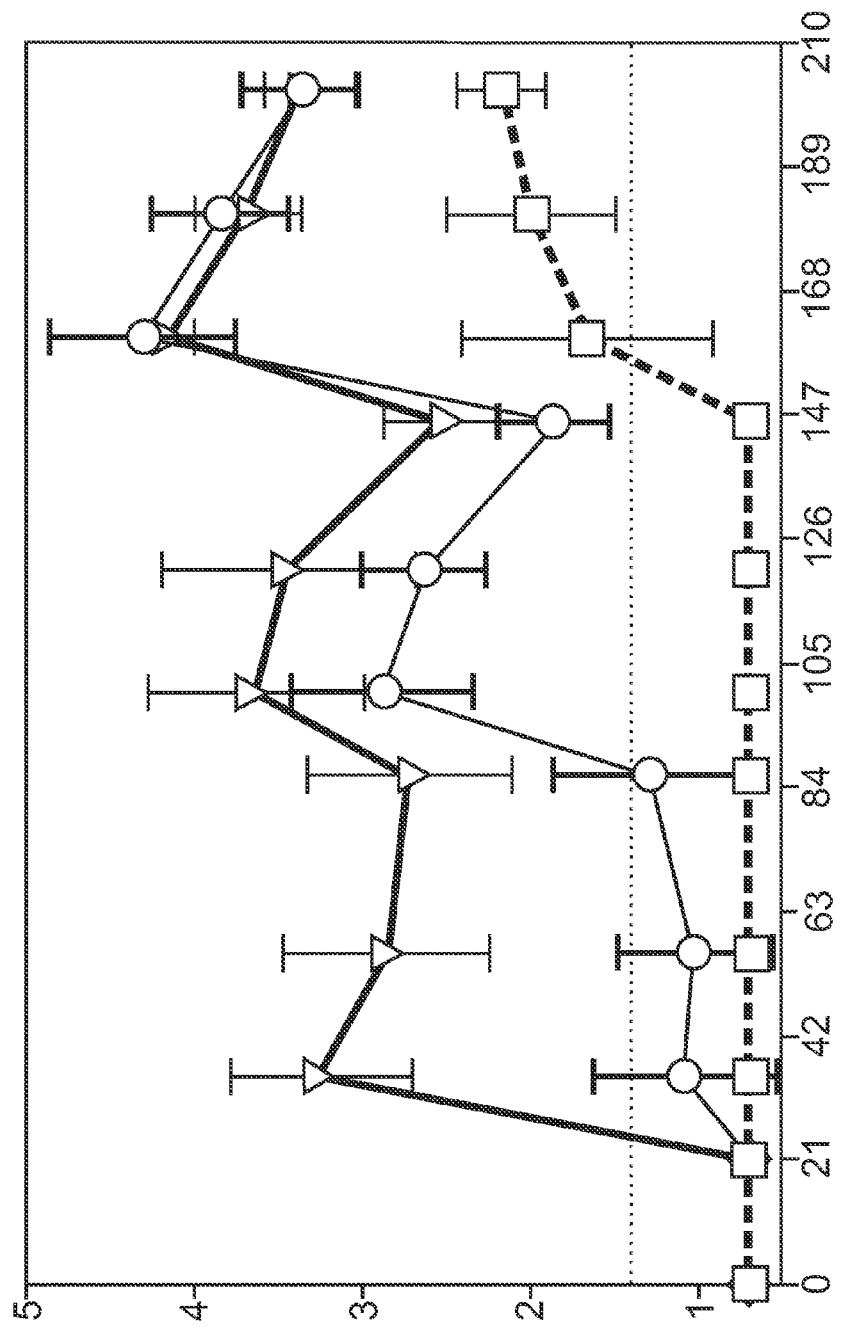
FIG. 14 shows F-specific IgG titers (mean $\log_{10}$ titers±std dev) over 210 days after immunisation of calves. The three lines are easily distinguished at day 63 and are, from bottom to top: PBS negative control; liposome-delivered RNA; and the "Triangle 4" product.
Figure 16A:
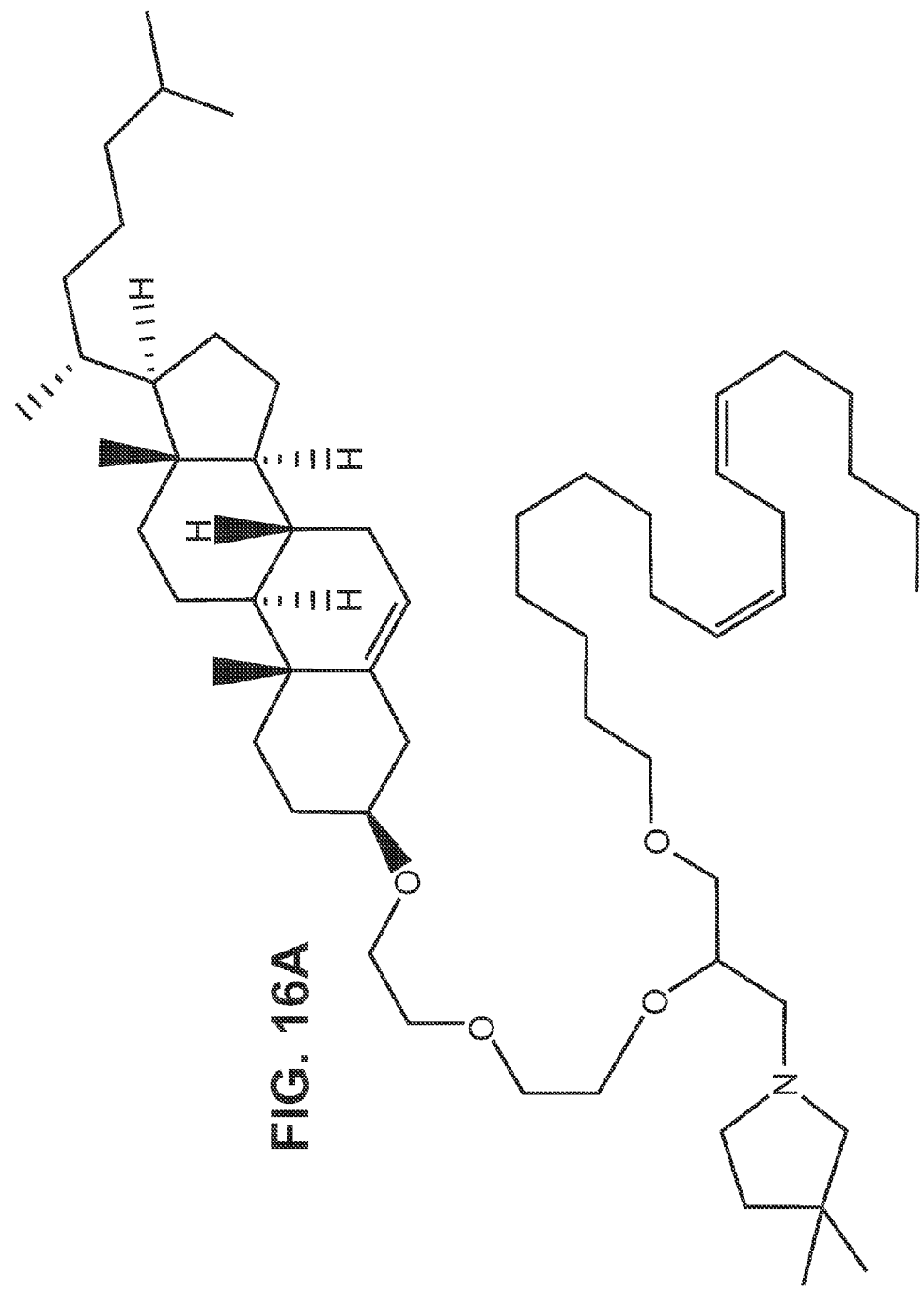
Figure 16B:
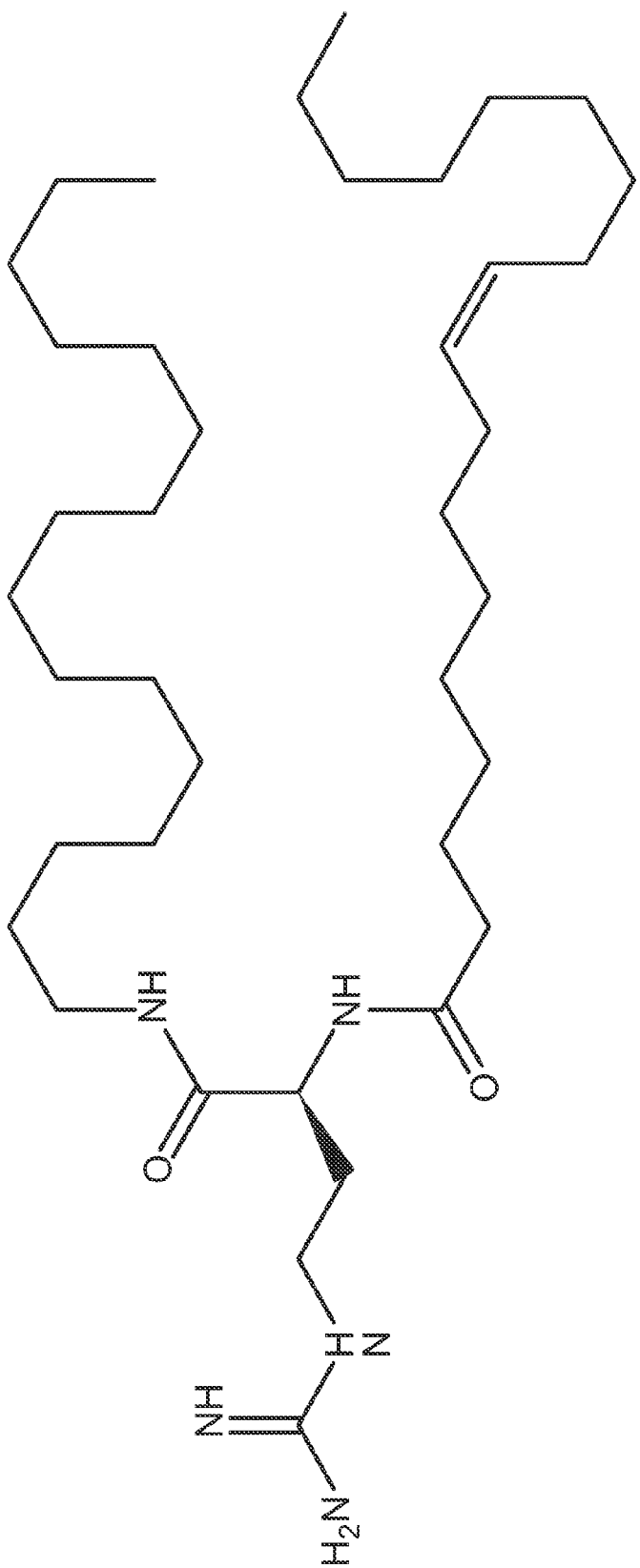
Figure 16C:
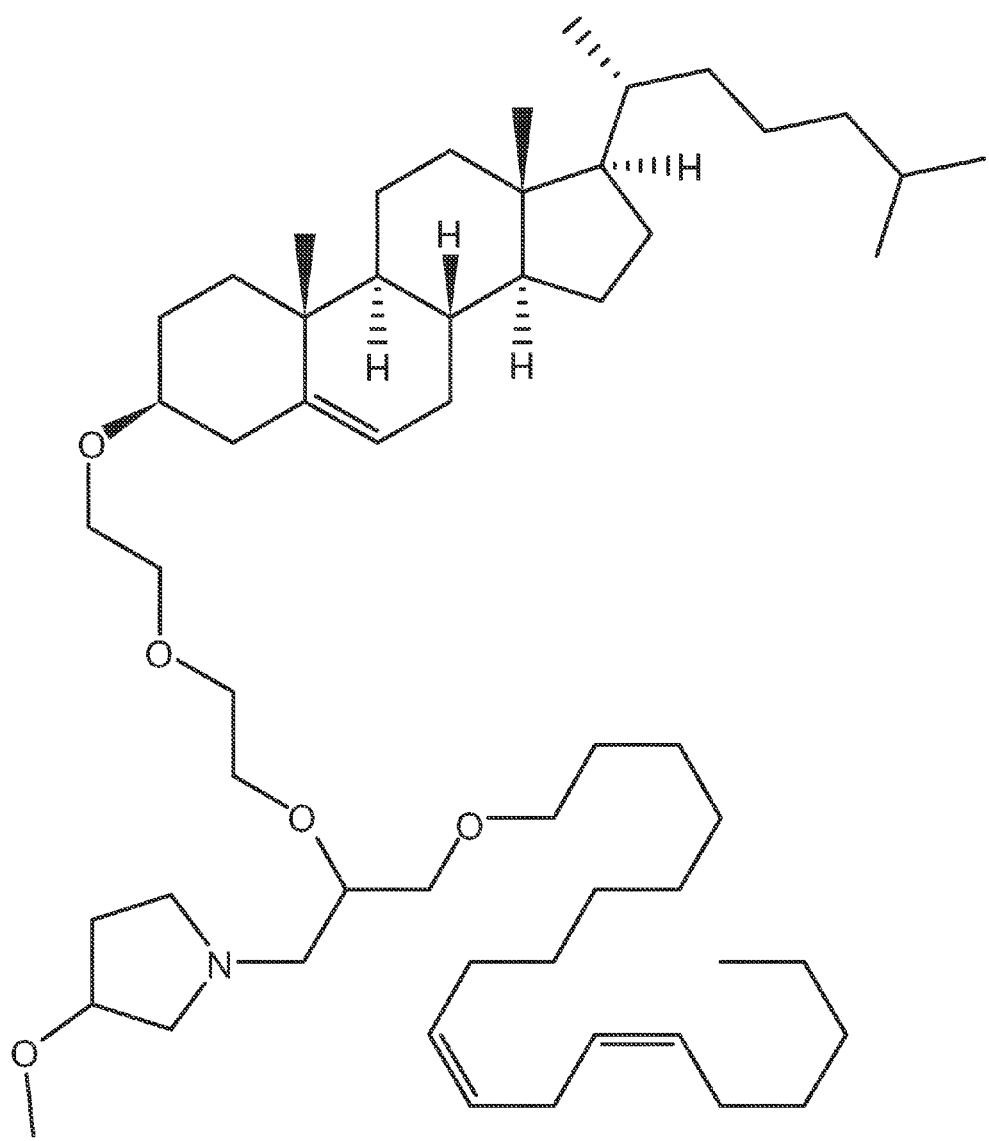
Figure 16D:
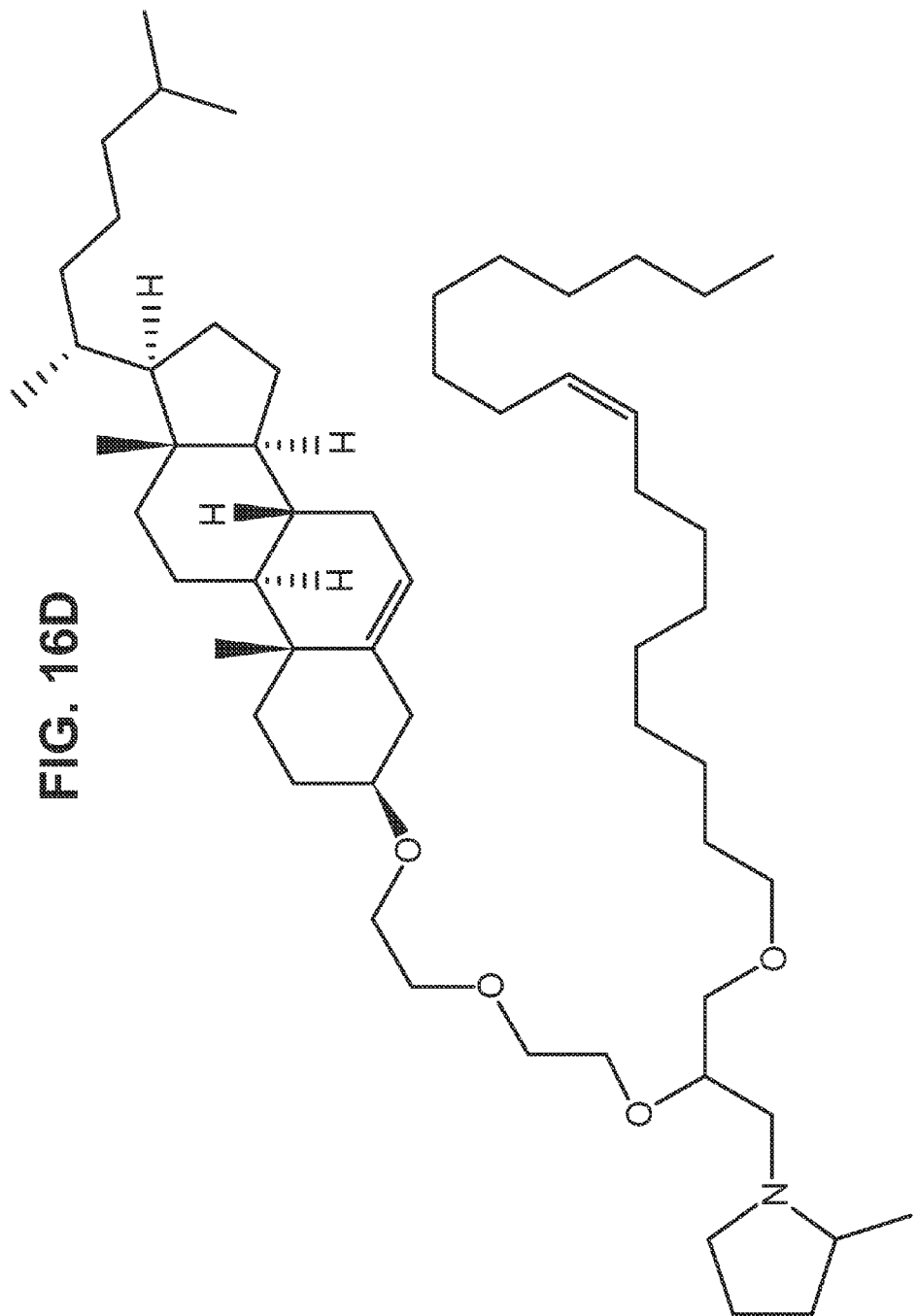
Figure 16E:
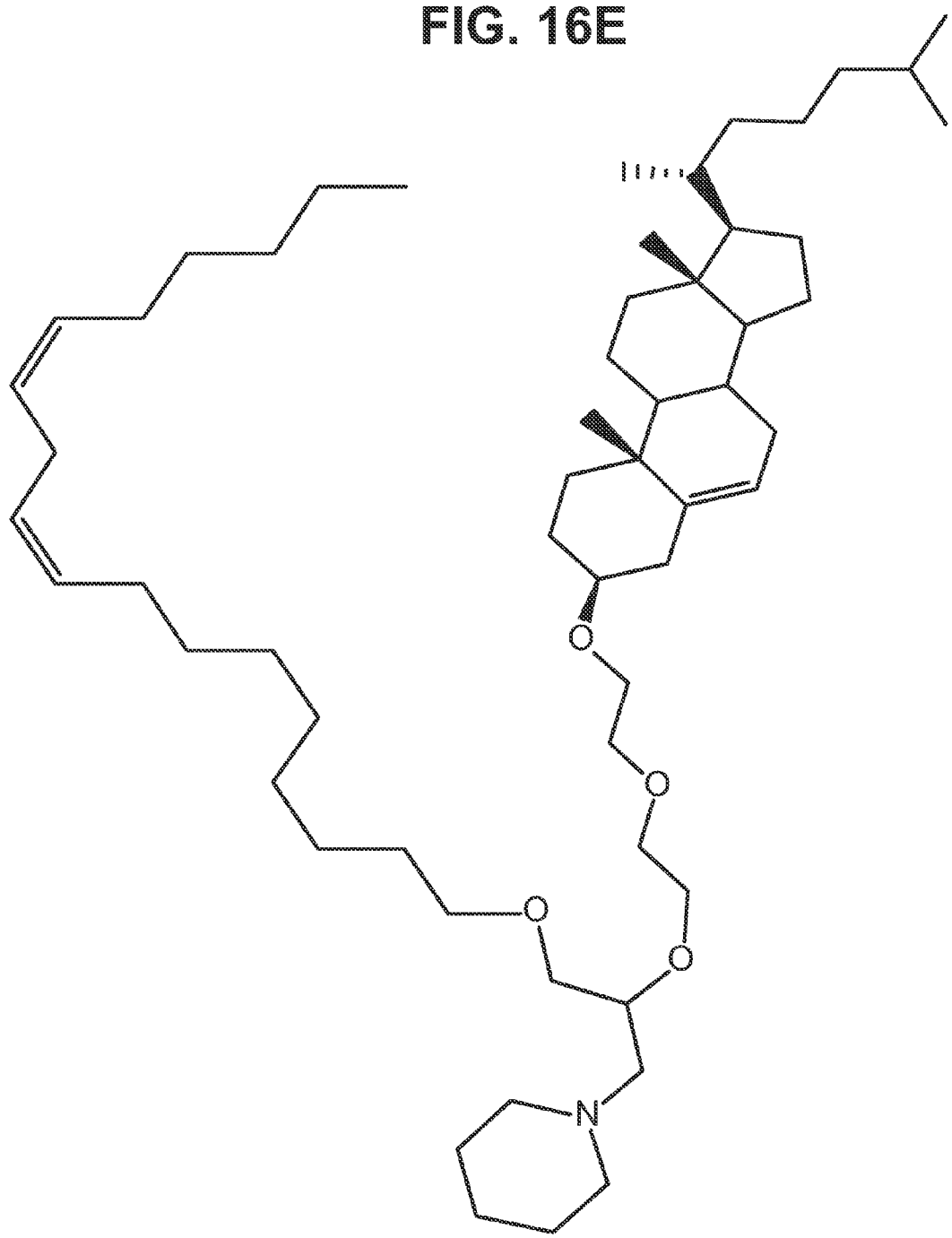
Figure 16H:
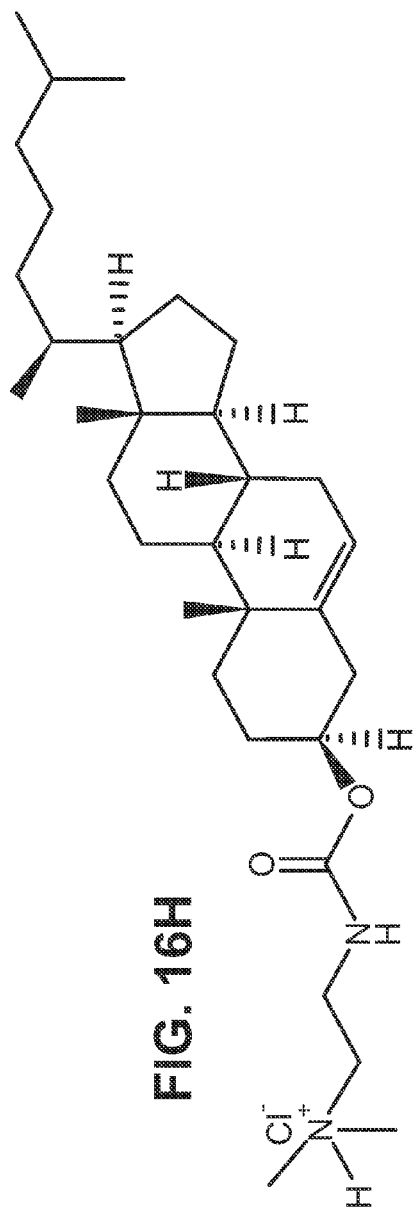
Figure 16I:
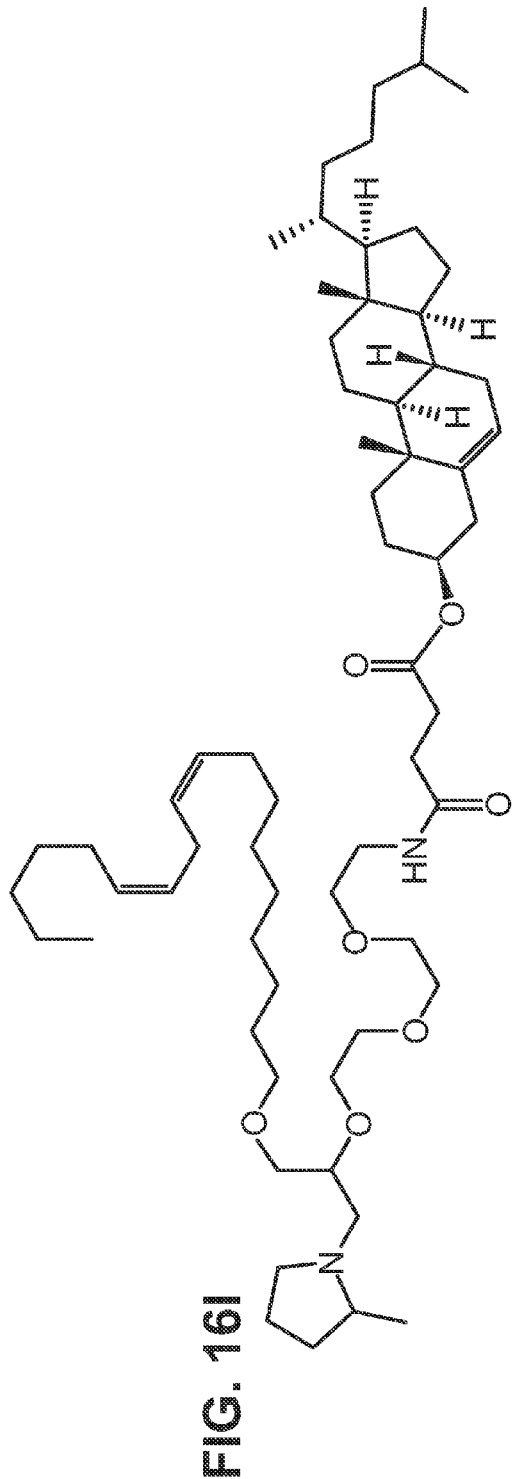
Figure 16J:
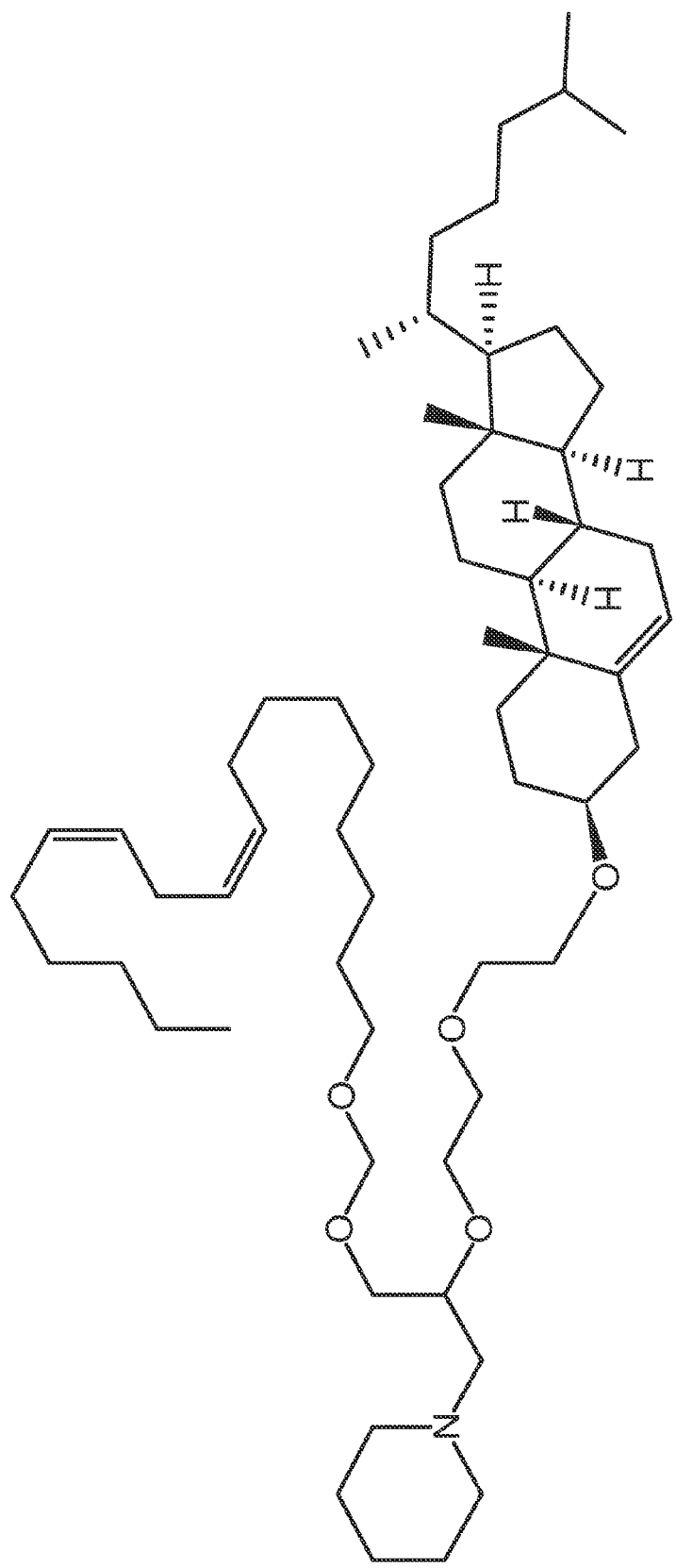
Figure 16K:
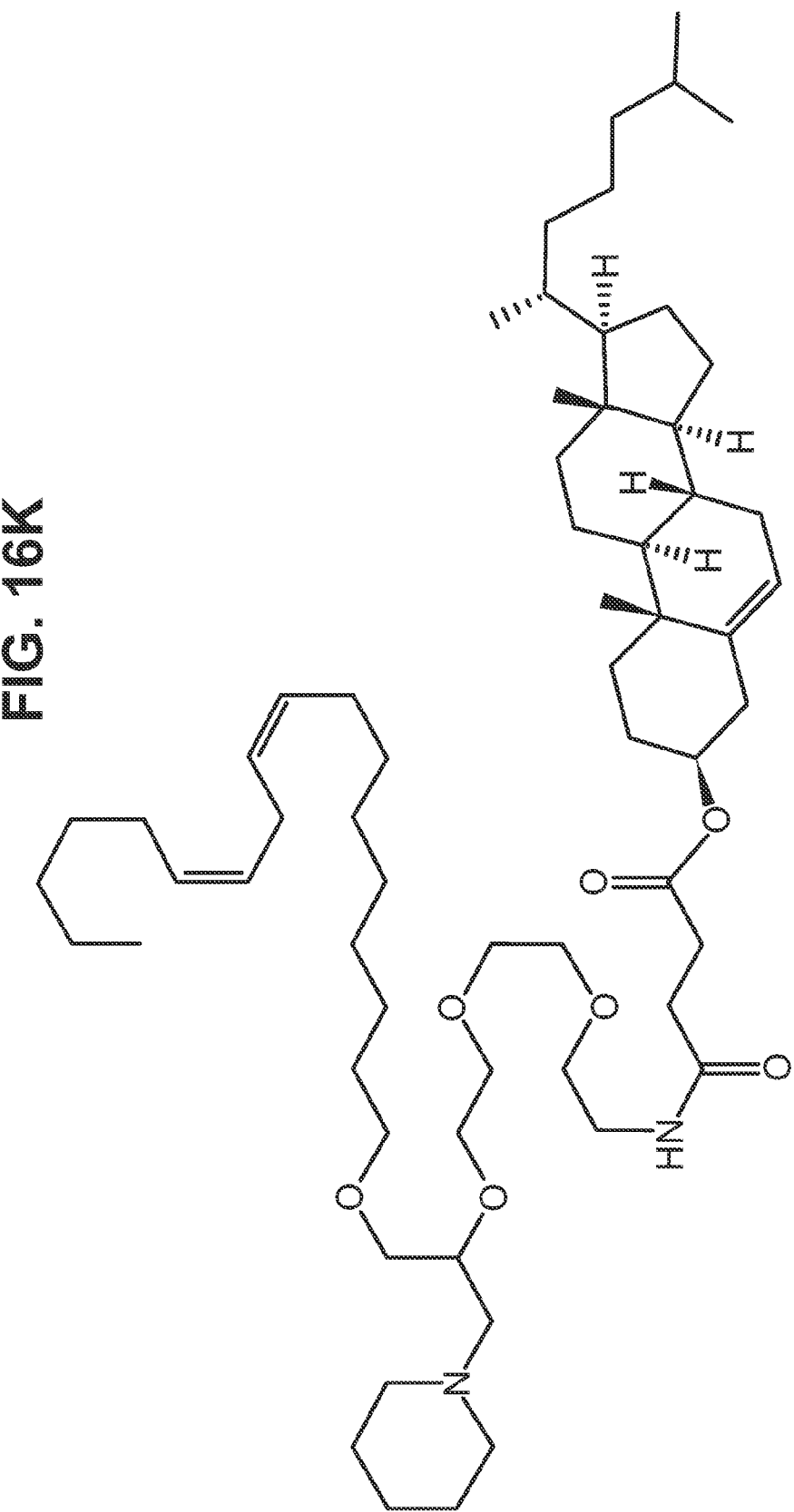

FIG. 14 shows F-specific IgG titers over 210 days. Over the first 63 days the RNA replicon was immunogenic in the cows via liposomes, although it gave lower titers than the licensed vaccine. All vaccinated cows showed F-specific antibodies after the second dose, and titers were very stable from the period of 2 to 6 weeks after the second dose (and were particularly stable for the RNA vaccines). Titres up to day 202 were as follows:

|            | D0 | 3wp1 D21 | 2wp2 D35 | 5wp2 D56 | ~9wp2 D86 | 2wp3 D100 | 5wp3 D121 | 8wp3 D146 | 2wp4 D160 | 5wp4 D181 | 8wp4 D202 |
| ---------- | -- | -------- | -------- | -------- | --------- | --------- | --------- | --------- | --------- | --------- | --------- |
| PBS        | 5  | 5        | 5        | 5        | 5         | 5         | 5         | 5         | 46        | 98        | 150       |
| Liposome   | 5  | 5        | 12       | 11       | 20        | 768       | 428       | 74        | 20774     | 7022      | 2353      |
| Triangle 4 | 5  | 5        | 1784     | 721      | 514       | 3406      | 2786      | 336       | 13376     | 4775      | 2133      |

RSV serum neutralizing antibody titers were as follows:

|            | D0 | 2wp2 D35 | 5wp2 D56 | 2wp3 D100 | 3wp3 D107 | 4wp3 D114 | 8wp3 D146 | 2wp4 D160 | 3wp4 D167 | 4wp4 D174 |
| ---------- | -- | -------- | -------- | --------- | --------- | --------- | --------- | --------- | --------- | --------- |
| PBS        | 12 | 10       | 10       | 14        | 18        | 20        | 14        | 10        | 10        | 10        |
| Liposome   | 13 | 10       | 10       | 20        | 13        | 17        | 13        | 47        | 26        | 21        |
| Triangle 4 | 12 | 15       | 13       | 39        | 38        | 41        | 13        | 24        | 26        | 15        |

The material used for the second liposome dose was not freshly prepared, and the same lot of RNA showed a decrease in potency in a mouse immunogenicity study. Therefore it is possible that the vaccine would have been more immunogenic if fresh material had been used for all vaccinations.

When assayed with complement, neutralizing antibodies were detected in all vaccinated cows. In this assay, all vaccinated calves had good neutralizing antibody titers after the second RNA vaccination Furthermore, the RNA vaccine elicited F-specific serum IgG titers that were detected in a few calves after the second vaccination and in all calves after the third.

MF59-adjuvanted RSV-F was able to boost the IgG response in all previously vaccinated calves, and to boost complement-independent neutralization titers of calves previously vaccinated with RNA.

Proof of concept for RNA vaccines in large animals is particularly important in light of the loss in potency observed previously with DNA-based vaccines when moving from small animal models to larger animals and humans. A typical dose for a cow DNA vaccine would be 0.5-1 mg [40, 41] and so it is very encouraging that immune responses were induced with only 66 µg of RNA.

Effect of Liposome Diameter

To obtain smaller liposomes the syringe/tube method was replaced by a method in which the lipid and RNA solutions are mixed in channels on a microfluidic chip.

Fresh lipid stock solutions in ethanol were prepared. 37 mg of DlinDMA, 11.8 mg of DSPC, 27.8 mg of cholesterol and 8.07 mg of PEG-DMG were weighed and dissolved in 7.55 mL of ethanol. The freshly prepared lipid stock solution was gently rocked at 37° C. for about 15 min to form a homogenous mixture. Then, 226.7 µL of the stock was added to 1.773 mL ethanol to make a working lipid stock solution of 2 mL. A 4 mL working solution of RNA was also prepared from a stock solution of ~1 µg/µL in 100 mM citrate buffer (pH 6). Four 20 mL glass vials (with stir bars) were rinsed with RNase Away solution and washed with plenty of MilliQ water before use to decontaminate the vials of RNAses. Two of the vials were used for the RNA working solution (2 mL in each vial) and the others for collecting the lipid and RNA mixes. The working lipid and RNA solutions were heated at 37° C. for 10 min before being loaded into 3 cc luer-lok syringes. Syringes containing RNA and the lipids were connected to a Mitos Droplet junction Chip (a glass microfluidic device obtained from Syrris, Part no. 3000158) using PTFE tubing 0.03 inches ID×1/16 inch OD, (Syrris) using a 4-way edge connector. Two RNA streams and one lipid stream were driven by syringe pumps and the mixing of the ethanol and aqueous phase was done at the X junction (100 µm×105 µm) of the chip. The flow rate of all three streams was kept at 1.5 mL/min, hence the ratio of total aqueous to ethanolic flow rate was 2:1. The tube outlet was positioned to collect the mixtures in a 20 mL glass vial (while stirring). The stir bar was taken out and the ethanol/aqueous solution was allowed to equilibrate to room temperature for 1 hour. Then the mixture was loaded in a 5 cc syringe which was fitted to a piece of PTFE tubing 0.03 inches ID×1/16 inches OD and in another 5 cc syringe with equal length of PTFE tubing, an equal volume of 100 mM citrate buffer (pH 6) was loaded. The two syringes were driven at 3 mL/min flow rate using a syringe pump and the final mixture collected in a 20 mL glass vial (while stirring). Next, liposomes were concentrated to 2 mL and dialyzed against 10-15 volumes of 1X PBS using the TFF system before recovering the final product. Hollow fiber filtration membranes with a 100 kDa pore size cutoff and 20 cm² surface area were used. For in vitro and in vivo experiments, formulations were diluted to the required RNA concentration with 1X PBS.

Whereas liposomes prepared using the syringe/tube method with 75 µg RNA had a Z average diameter of 148 nm and a polydispersity index of 0.122, the chip mixing gave liposomes with a Z average diameter of 97 nm and a polydispersity index of 0.086. The proportion of encapsulated RNA decreased slightly from 90% to 87%. These diameters and polydispersity indices were measured using a Zetasizer Nano ZS (Malvern Instruments, Worcestershire, UK) according to the manufacturer's instructions. Liposomes were diluted in 1X PBS before measurement.

The liposomes were administered to 8-10 week old BALB/c mice by intramuscular injection on day 0, 50 µl per leg. Sinus orbital bleeds were taken on days 1&3, and a terminal bleed on day 6. Serum SEAP levels were measured by chemiluminescent assay. As shown in FIG. 3, the smaller liposomes increased SEAP levels by ~2-fold at day 1 and by ~5-fold at day 6.

Liposomes prepared by the two different methods were also assessed for delivery of a replicon encoding full-length RSV-F protein. F-specific serum IgG titers of mice, 8 animals per group, were measured after intramuscular vaccinations on days 0 and 21. Sera were collected for antibody analysis on days 14 (2wp1) and 35 (2wp2). If an individual animal had a titer of <25 (limit of detection) it was assigned a titer of 5. Data are shown below as geometric mean titers of each group:

| Formulation | Naked | Syringe/tube liposomes | Chip liposomes |
|---|---|---|---|
| 2wp1 GMT | 35 | 2421 | 4695 |
| 2wp2 GMT | 457 | 10757 | 19773 |

Thus the smaller chip-mixed liposomes gave ~2-fold higher GMTs at 2wp1 and 2wp2.

Various different liposomes with different diameters were also used to deliver a replicon encoding full-length RSV F protein. Total IgG titers against F protein two weeks after the first dose are plotted against liposome diameter in FIG. 15.

Liposome Manufacturing Methods

In general, eight different methods have been used for preparing liposomes according to the invention. These are referred to in the text as methods (A) to (H) and they differ mainly in relation to filtration and TFF steps. Details are as follows:

(A) Fresh lipid stock solutions in ethanol were prepared. 37 mg of DlinDMA, 11.8 mg of DSPC, 27.8 mg of Cholesterol and 8.07 mg of PEG DMG 2000 were weighed and dissolved in 7.55 mL of ethanol. The freshly prepared lipid stock solution was gently rocked at 37° C. for about 15 min to form a homogenous mixture. Then, 755 µL of the stock was added to 1.245 mL ethanol to make a working lipid stock solution of 2 mL. This amount of lipids was used to form liposomes with 250 µg RNA. A 2 mL working solution of RNA was also prepared from a stock solution of ~1 µg/µL in 100 mM citrate buffer (pH 6). Three 20 mL glass vials (with stir bars) were rinsed with RNase Away solution (Molecular BioProducts, San Diego, Calif.) and washed with plenty of MilliQ water before use to decontaminate the vials of RNases. One of the vials was used for the RNA working solution and the others for collecting the lipid and RNA mixes (as described later). The working lipid and RNA solutions were heated at 37° C. for 10 min before being loaded into 3 cc luer-lok syringes. 2 mL of citrate buffer (pH 6) was loaded in another 3 cc syringe. Syringes containing RNA and the lipids were connected to a T mixer (PEEK™ 500 μm ID junction, Idex Health Science, Oak Harbor, Wash.) using FEP tubing (fluorinated ethylene-propylene; al FEP tubing has a 2 mm internal diameter×3 mm outer diameter, supplied by Idex Health Science). The outlet from the T mixer was also FEP tubing. The third syringe containing the citrate buffer was connected to a separate piece of FEP tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 hour. 4 ml of the mixture was loaded into a 5 cc syringe, which was connected to a piece of FEP tubing and in another 5 cc syringe connected to an equal length of FEP tubing, an equal amount of 100 mM citrate buffer (pH 6) was loaded. The two syringes were driven at 7 mL/min flow rate using the syringe pump and the final mixture collected in a 20 mL glass vial (while stirring). Next, the mixture collected from the second mixing step (liposomes) were passed through a Mustang Q membrane (an anion-exchange support that binds and removes anionic molecules, obtained from Pall Corporation, Ann Arbor, Mich., USA). Before passing the liposomes, 4 mL of 1 M NaOH, 4 mL of 1 M NaCl and 10 mL of 100 mM citrate buffer (pH 6) were successively passed through the Mustang membrane. Liposomes were warmed for 10 min at 37° C. before passing through the membrane. Next, liposomes were concentrated to 2 mL and dialyzed against 10-15 volumes of 1X PBS using TFF before recovering the final product. The TFF system and hollow fiber filtration membranes were purchased from Spectrum Labs and were used according to the manufacturer's guidelines. Polysulfone hollow fiber filtration membranes (part number P/N: X1AB-100-20P) with a 100 kD pore size cutoff and 8 cm$^2$ surface area were used. For in vitro and in vivo experiments, formulations were diluted to the required RNA concentration with 1X PBS.

(B) As method (A) except that, after rocking, 226.7 μL of the stock was added to 1.773 mL ethanol to make a working lipid stock solution of 2 mL, thus modifying the lipid:RNA ratio.

(C) As method (B) except that the Mustang filtration was omitted, so liposomes went from the 20 mL glass vial into the TFF dialysis.

(D) As method (C) except that the TFF used polyethersulfone (PES) hollow fiber membranes (part number P-C1-100E-100-01N) with a 100 kD pore size cutoff and 20 cm$^2$ surface area.

(E) As method (D) except that a Mustang membrane was used, as in method (A).

(F) As method (A) except that the Mustang filtration was omitted, so liposomes went from the 20 mL glass vial into the TFF dialysis.

(G) As method (D) except that a 4 mL working solution of RNA was prepared from a stock solution of ~1 μg/μL in 100 mM citrate buffer (pH 6). Then four 20 mL glass vials were prepared in the same way. Two of them were used for the RNA working solution (2 mL in each vial) and the others for collecting the lipid and RNA mixes, as in (C). Rather than use T mixer, syringes containing RNA and the lipids were connected to a Mitos Droplet junction Chip (a glass microfluidic device obtained from Syrris, Part no. 3000158) using PTFE tubing (0.03 inches internal diameter×1/16 inch outer diameter) using a 4-way edge connector (Syrris). Two RNA streams and one lipid stream were driven by syringe pumps and the mixing of the ethanol and aqueous phase was done at the X junction (100 μm×105 μm) of the chip. The flow rate of all three streams was kept at 1.5 mL/min, hence the ratio of total aqueous to ethanolic flow rate was 2:1. The tube outlet was positioned to collect the mixtures in a 20 mL glass vial (while stirring). The stir bar was taken out and the ethanol/aqueous solution was allowed to equilibrate to room temperature for 1 h. Then the mixture was loaded in a 5 cc syringe, which was fitted to another piece of the PTFE tubing; in another 5 cc syringe with equal length of PTFE tubing, an equal volume of 100 mM citrate buffer (pH 6) was loaded. The two syringes were driven at 3 mL/min flow rate using a syringe pump and the final mixture collected in a 20 mL glass vial (while stirring). Next, liposomes were concentrated to 2 mL and dialyzed against 10-15 volumes of 1X PBS using TFF, as in (D).

(H) As method (A) except that the 2 mL working lipid stock solution was made by mixing 120.9 μL of the lipid stock with 1.879 mL ethanol. Also, after mixing in the T mixer the liposomes from the 20 mL vial were loaded into Pierce Slide-A-Lyzer Dialysis Cassette (Thermo Scientific, extra strength, 0.5-3 mL capacity) and dialyzed against 400-500 mL of 1X PBS overnight at 4° C. in an autoclaved plastic container before recovering the final product.

RSV Immunogenicity

The vA317 self-replicating replicon encoding RSV F protein was administered to BALB/c mice, 4 or 8 animals per group, by bilateral intramuscular vaccinations (50 μL per leg) on days 0 and 21 with the replicon (1 μg) alone or formulated as liposomes with DlinDMA ("RV01") or DOTAP ("RV13") or the lipid shown in FIGS. 16A to 16M ("RV05"). The RV01 liposomes had 40% DlinDMA, 10% DSPC, 48% cholesterol and 2% PEG-DMG, but with differing amounts of RNA. The RV05 liposomes had either 40% RV05, 10% DSPC, 48% cholesterol and 2% PEG-DMG or 60% RV05, 38% cholesterol and 2% PEG-DMG. The RV13 liposomes had 40% DOTAP, 10% DOPE, 48% cholesterol and 2% PEG-DMG. For comparison, naked plasmid DNA (20 μg) expressing the same RSV-F antigen was delivered either using electroporation or with RV01(10) liposomes (0.1 μg DNA). Four mice were used as a naïve control group.

Liposomes were prepared by method (A) or method (B). For some liposomes made by method (A) a double or half amount of RNA was used. Z average particle diameter and polydispersity index were:

| RV | Zav (nm) | pdI | Preparation |
| --- | --- | --- | --- |
| RV01 (10) | 158.6 | 0.088 | (A) |
| RV01 (08) | 156.8 | 0.144 | (A) |
| RV01 (05) | 136.5 | 0.136 | (B) |
| RV01 (09) | 153.2 | 0.067 | (A) |
| RV01 (10) | 134.7 | 0.147 | (A) |
| RV05 (01) | 148 | 0.127 | (A) |
| RV05 (02) | 177.2 | 0.136 | (A) |
| RV13 (02) | 128.3 | 0.179 | (A) |

Serum was collected for antibody analysis on days 14, 36 and 49. Spleens were harvested from mice at day 49 for T cell analysis.

F-specific serum IgG titers (GMT) were as follows:

| RV | Day 14 | Day 36 |
|---|---|---|
| Naked DNA plasmid | 439 | 6712 |
| Naked A317 RNA | 78 | 2291 |
| RV01 (10) | 3020 | 26170 |
| RV01 (08) | 2326 | 9720 |
| RV01 (05) | 5352 | 54907 |
| RV01 (09) | 4428 | 51316 |
| RV05 (01) | 1356 | 5346 |
| RV05 (02) | 961 | 6915 |
| RV01 (10) DNA | 5 | 13 |
| RV13 (02) | 644 | 3616 |

The proportion of T cells which are cytokine-positive and specific for RSV F51-66 peptide are as follows, showing only figures which are statistically significantly above zero:

| RV | CD4+CD8− | | | | CD4−CD8+ | | | |
|---|---|---|---|---|---|---|---|---|
|  | IFNγ | IL2 | IL5 | TNFα | IFNγ | IL2 | IL5 | TNFα |
| Naked DNA plasmid | 0.04 | 0.07 |  | 0.10 | 0.57 | 0.29 |  | 0.66 |
| Naked A317 RNA | 0.04 | 0.05 |  | 0.08 | 0.57 | 0.23 |  | 0.67 |
| RV01 (10) | 0.07 | 0.10 |  | 0.13 | 1.30 | 0.59 |  | 1.32 |
| RV01 (08) | 0.02 | 0.04 |  | 0.06 | 0.46 | 0.30 |  | 0.51 |
| RV01 (05) | 0.08 | 0.12 |  | 0.15 | 1.90 | 0.68 |  | 1.94 |
| RV01 (09) | 0.06 | 0.08 |  | 0.09 | 1.62 | 0.67 |  | 1.71 |
| RV01 (10) DNA |  |  |  | 0.03 |  |  |  | 0.08 |
| RV13 (02) | 0.03 | 0.04 |  | 0.06 | 1.15 | 0.41 |  | 1.18 |

Thus the liposome formulations significantly enhanced immunogenicity relative to the naked RNA controls, as determined by increased F-specific IgG titers and T cell frequencies. Plasmid DNA formulated with liposomes, or delivered naked using electroporation, was significantly less immunogenic than liposome-formulated self-replicating RNA.

Further RV01 liposomes were prepared by method (H), using either short (2 kDa) or long (5 kDa) PEG conjugated to the DMG, and either encapsulating 150 μg RNA (vA375 replicon encoding surface fusion glycoprotein of RSV) or encapsulating only buffer. Thus these liposomes had 40% DlinDMA, 10% DSPC, 48% Chol, and 2% PEG-DMG. Sizes and encapsulation were as follows:

| RV | PEG | Zav (nm) | pdI | RNA | Encapsulat" |
|---|---|---|---|---|---|
| RV01 (36) | 2 kDa | 152.1 | 0.053 | + | 92.5% |
| RV01 (36) | 2 kDa | 144 | 0.13 | − | — |
| RV01 (43) | 5 kDa | 134 | 0.136 | + | 71.6% |
| RV01 (43) | 5 kDa | 130.3 | 0.178 | − | — |

The liposomes were administered to BALB/c mice (10 per group) by bilateral intramuscular injection (50 μl per leg) on days 0 & 21. Doses were 0.01, 0.03, 0.1, 0.3 or 1 μg. F-specific serum IgG and PRNT60 titers (GMT) were as follows, 2 weeks after the first or second injection:

| RV | RNA (μg) | 2wp1 | 2wp2 | PRNT60 (2wp2) |
|---|---|---|---|---|
| Buffer control | 0 | — | — | 10 |
| RV01 (36) | 0 | — | — | 10 |
| RV01 (36) | 0.01 | 3399 | 50691 | 37 |
| RV01 (36) | 0.03 | 3446 | 53463 | 83 |
| RV01 (36) | 0.1 | 8262 | 76808 | 238 |
| RV01 (36) | 0.3 | 5913 | 82599 | 512 |
| RV01 (36) | 1 | 8213 | 85138 | 441 |
| RV01 (43) | 0 | — | — | 10 |
| RV01 (43) | 0.01 | 3959 | 37025 | 51 |
| RV01 (43) | 0.03 | 5842 | 50763 | 180 |
| RV01 (43) | 0.1 | 7559 | 122555 | 314 |
| RV01 (43) | 0.3 | 5712 | 126619 | 689 |
| RV01 (43) | 1 | 9434 | 199991 | 1055 |

Liposomes—Requirement for Encapsulation

As mentioned above, with reference to FIG. 10, encapsulation is essential for potent expression. Further experiments used three different RNAs: (i) 'vA317' replicon that expresses RSV-F i.e. the surface fusion glycoprotein of RSV; (ii) 'vA17' replicon that expresses GFP; and (iii) 'vA336' that is replication-defective and encodes GFP. RNAs were delivered either naked or with liposomes made by method (D). Empty liposomes were made by method (D) but without any RNA. Liposome formulations had these characteristics:

| RNA | Particle Size Zav (nm) | Polydispersity | RNA Encapsulation |
|---|---|---|---|
| vA317 | 155.7 | 0.113 | 86.6% |
| vA17 | 148.4 | 0.139 | 92% |
| vA336 | 145.1 | 0.143 | 92.9% |
| Empty | 147.9 | 0.147 | — |

BALB/c mice, 5 animals per group, were given bilateral intramuscular vaccinations (50 μL per leg) on days 0 and 21 with:

Group 1 naked self-replicating RSV-F RNA (vA317, 0.1 μg)

Group 2 self-replicating RSV-F RNA (vA317, 0.1 μg) encapsulated in liposomes

Group 3 self-replicating RSV-F RNA (vA317, 0.1 μg) added to empty liposomes

Group 4 F subunit protein (5 μg)

Serum was collected for antibody analysis on days 14, 35 and 51. F-specific specific serum IgG titers (GMT) were measured; if an individual animal had a titer of <25 (limit of detection), it was assigned a titer of 5. In addition, spleens were harvested from mice at day 51 for T cell analysis, to determine cells which were cytokine-positive and specific for RSV F51-66 peptide (CD4+) or for RSV F peptides F85-93 and F249-258 (CD8+).

IgG titers were as follows in the 10 groups and in non-immunised control mice:

| Day | 1 | 2 | 3 | 4 | — |
|---|---|---|---|---|---|
| 14 | 22 | 1819 | 5 | 5 | 5 |
| 35 | 290 | 32533 | 9 | 19877 | 5 |
| 51 | 463 | 30511 | 18 | 20853 | 5 |

RSV serum neutralization titers at day 51 were as follows:

| Day | 1 | 2 | 3 | 4 |
|---|---|---|---|---|
| 51 | 35 | 50 | 24 | 38 |

Animals showing RSV F-specific CD4+ splenic T cells on day 51 were as follows, where a number (% positive cells) is given only if the stimulated response was statistically significantly above zero:

| Cytokine | 1 | 2 | 3 | 4 |
|---|---|---|---|---|
| IFN-γ |  | 0.04 |  |  |
| IL2 | 0.02 | 0.06 |  | 0.02 |
| IL5 |  |  |  |  |
| TNFα | 0.03 | 0.05 |  |  |

Animals showing RSV F-specific CD8+ splenic T cells on day 51 were as follows, where a number is given only if the stimulated response was statistically significantly above zero:

| Cytokine | 1 | 2 | 3 | 4 |
|---|---|---|---|---|
| IFN-γ | 0.37 | 0.87 |  |  |
| IL2 | 0.11 | 0.40 |  | 0.04 |
| IL5 |  |  |  |  |
| TNFα | 0.29 | 0.79 |  | 0.06 |

Thus encapsulation of RNA within the liposomes is necessary for high immunogenicity, as a simple admixture of RNA and the liposomes (group 3) was not immunogenic (in fact, less immunogenic than naked RNA).

Different Cationic Lipids with vA317 RSV Replicon

Further experiments compared four different cationic lipids (DlinDMA, RV02, RV04 & RV07). All liposomes contained 2% PEG-DMG 2000 but remaining lipid compositions varied. The compositions and physical characteristics were as follows:

| Name | Lipid 1 | Other lipids | Zav diam (nm) | pdI | % encap" |
|---|---|---|---|---|---|
| A | DlinDMA, 40% | 10% DSPC, 48% cholesterol | 158.6 | 0.088 | 90.7 |
| B | RV02, 40% | 10% DSPC, 48% cholesterol | 146.8 | 0.084 | 97.5 |
| C | RV04, 40% | 10% DSPC, 48% cholesterol | 136.7 | 0.165 | 67.3 |
| D | RV04, 60% | 38% cholesterol | 176.3 | 0.157 | 55.2 |
| E | RV07, 40% | 10% DSPC, 48% cholesterol | 144.9 | 0.204 | 82 |
| F | RV07, 60% | 38% cholesterol | 124.1 | 0.195 | 80 |

BALB/c mice, 8 per group, were given bilateral intramuscular vaccinations (50 μL per leg) on days 0 and 21 with naked replicon (1 μg) or 0.1 μg encapsulated RNA. F-specific serum IgG titers (GMT) 2 weeks after these two injections were as follows:

| Liposomes | Day 14 | Day 35 |
|---|---|---|
| Naked A317 RNA | 111 | 469 |
| A | 1834 | 30519 |
| B | 1050 | 5681 |
| C | 430 | 4127 |
| D | 779 | 4693 |
| E | 586 | 6424 |
| F | 121 | 2568 |

For RV07 the absence of DSPC caused a large decrease in immunogenicity.

Further lipids (RV03, RV08, RV09, RV14 [42]) were tested in the same way:

| Name | Lipid 1 | Other lipids | Zav diam (nm) | pdI | % encap" |
|---|---|---|---|---|---|
| G | DlinDMA, 40% | 10% DSPC, 48% cholesterol | 158.6 | 0.088 | 90.7 |
| H | RV03, 40% | 10% DSPC, 48% cholesterol | 150.3 | 0.188 | 83.1 |
| I | RV03, 60% | 38% cholesterol | 161.1 | 0.239 | 68.4 |
| J | RV08, 40% | 10% DSPC, 48% cholesterol | 191.1 | 0.227 | 51.7 |
| K | RV09, 40% | 10% DSPC, 48% cholesterol | 161.6 | 0.209 | 64.5 |
| L | RV09, 60% | 38% cholesterol | 170.7 | 0.121 | 82.4 |
| M | RV14, 60% | 30% DSPC | 155.5 | 0.238 | 63.3 |
| N | RV01, 40% | 10% DSPC, 48% cholesterol | 96.14 | 0.087 | 92 |

| Liposomes | Day 14 | Day 35 |
|---|---|---|
| Naked A317 RNA | 35 | 457 |
| G | 2421 | 10757 |
| H | 15 | 52 |
| I | 16 | 85 |
| J | 991 | 1921 |
| K | 1082 | 1421 |
| L | 146 | 286 |
| M | 27 | 212 |
| N | 4695 | 19773 |

Liposome M (with DC-cholesterol) performed poorly, even below the naked RNA control. In contrast, the remaining cationic lipids gave useful results. Liposome N was prepared by a different mixing method (method (G) with a microfluidic chip) from liposome G (method (D)) and this smaller liposome gave better results with approximately the same encapsulation.

Further lipids (RV01, RV10, RV11, RV15) were tested in the same way:

| Name | Lipid 1 | Other lipids | Zav diam (nm) | pdI | % encap" |
|---|---|---|---|---|---|
| P | DlinDMA, 40% | 10% DSPC, 48% cholesterol | 158.6 | 0.088 | 90.7 |
| Q | RV10, 40% | 10% DSPC, 48% cholesterol | 123.6 | 0.14 | 80.3 |
| R | RV11, 40% | 10% DSPC, 48% cholesterol | 137.1 | 0.155 | 81 |
| S | RV11, 60% | 38% cholesterol | 135.4 | 0.175 | 79.7 |
| T | RV15, 40% | 38% cholesterol | 111 | 0.167 | 76.4 |

| Liposomes | Day 14 | Day 35 |
|---|---|---|
| Naked A317 RNA | 185 | 982 |
| P | 2787 | 27416 |
| Q | 24 | 161 |
| R | 633 | 1715 |
| S | 405 | 2733 |
| T | 761 | 2459 |

Except for liposome Q each of these liposomes performed better than the control. The RV10 lipid in liposome Q has a pKa of 7.86 which seems too high to be useful in vivo. Even inside the useful pKa range of 5.0 to 7.6, however, although results were good, none of the lipids with one alkyl tail and one steroid-containing tail gave results as good as RV01.

Further liposomes were made with RV05. The liposomes all had 40% RV05 and 2% PEGylated lipid, but the remaining components varied (although cholesterol was always included). Physical characteristics were:

| Name | PEGylated lipid | Other components | Zav (nm) | pdI | % encapsul[n] |
|---|---|---|---|---|---|
| U | DMG | 10% DSPC, 48% chol | 102.2 | 0.12 | 76.81 |
| V | Cholesterol | 10% DSPC, 46% chol, 2% αGC | 103.7 | 0.107 | 72.58 |
| W | DMG | 10% DPyPE, 48% chol | 99.6 | 0.115 | 78.34 |
| X | DMG | 10% 18:3 PC, 48% chol | 130 | 0.14 | 87.92 |
| Y | DMG | 10% 18:2 PC, 48% chol | 101.1 | 0.133 | 76.64 |
| Z | DMG | 30% 18:2 PC, 28% chol | 134.3 | 0.158 | 57.76 |

αGC = α-galactosylceramide

BALB/c mice were tested as before:

| Injection | Day 14 | Day 35 |
|---|---|---|
| Naked RNA | 321 | 915 |
| U | 551 | 955 |
| V | 342 | 2531 |
| W | 1127 | 3881 |
| X | 364 | 1741 |
| Y | 567 | 5679 |
| Z | 1251 | 5303 |

For a cationic lipid with an asymmetrical lipid tails (alkyl+cholesterol), changing the neutral lipid from DSPC (saturated C18 lipid tail) to 18:2 or 18:3 PC (with 2 and 3 unsaturated double bonds per tail) increased total IgG titers. Comparable results were observed by replacing DSPC with DPyPE.

Further Different Cationic Lipids with vA317 RSV Replicon

Cationic lipids disclosed in reference 43 were also used for preparing liposomes for the vA317 replicon. These cationic lipids have a pKa between 5.8 and 6.1. For comparison DODMA, DlinDMA and DOTMA were also tested. Cationic lipid was always present at 40%. All liposomes included cholesterol and 2% PEGylated DMG (PEG2000, except liposomes E which had PEG5000) and were made by method (H). Physical characteristics were as follows:

| | Cationic lipid | Other lipids | Zav (nm) | pdI | Encaps[n] % |
|---|---|---|---|---|---|
| A | DlinDMA | 10% DSPC, 48% chol | 122.3 | 0.068 | 95.23 |
| B | RV16 | 10% DSPC, 48% chol | 148.5 | 0.088 | 69.34 |
| C | RV17 | 10% DSPC, 48% chol | 138 | 0.098 | 67.99 |
| D | DODMA | 10% DSPC, 48% chol | 107.4 | 0.151 | 96.61 |
| E | DlinDMA | 10% DSPC, 48% chol | 106.1 | 0.136 | 61.61 |
| F | DOTMA | 10% DSPC, 48% chol | 89.32 | 0.164 | 98.87 |
| G | DlinDMA | 10% 18:2 PC, 48% chol | 115.8 | 0.111 | 95.67 |
| H | DlinDMA | 10% LPC, 48% chol | 116.7 | 0.143 | 94.84 |
| I | DlinDMA | 10% DPyPE, 48% chol | 134 | 0.163 | 96.33 |
| J | RV05 | 10% 18:2 PC, 8% chol, 40% DPyPE | 124.7 | 0.17 | 61.51 |

These liposomes were used to vaccinate BALB/c mice as before. F-specific serum IgG titers (GMT) were as follows:

| Group | Day 14 | Day 35 |
|---|---|---|
| Naked RNA | 28 | 721 |
| A | 2237 | 12407 |
| B | 1107 | 13981 |
| C | 2109 | 22147 |
| D | 2175 | 24881 |
| E | 5654 | 39927 |
| F | 285 | 6362 |
| G | 1058 | 3467 |
| H | 1475 | 10211 |
| I | 557 | 1363 |
| J | 703 | 1732 |

Thus the RV05 liposomes were more immunogenic than naked RNA, but less immunogenic than RV01 liposomes.

Spleens were harvested at day 49 for T cell analysis. All liposomes gave F-specific cytokine-positive T cell frequencies (CD4+ and CD8+) which were statistically significantly above zero.

Different Lipids and PEG Lengths

The vA317 replicon was administered in liposomes having a variety of different lipids with different PEG lengths. The liposomes all had 40% DlinDMA, 10% DSPC and 48% cholesterol, but the remaining 2% was varied, with different PEGylated lipids (e.g. FIGS. 18A to 18E) and different PEG lengths.

Figure 18A:
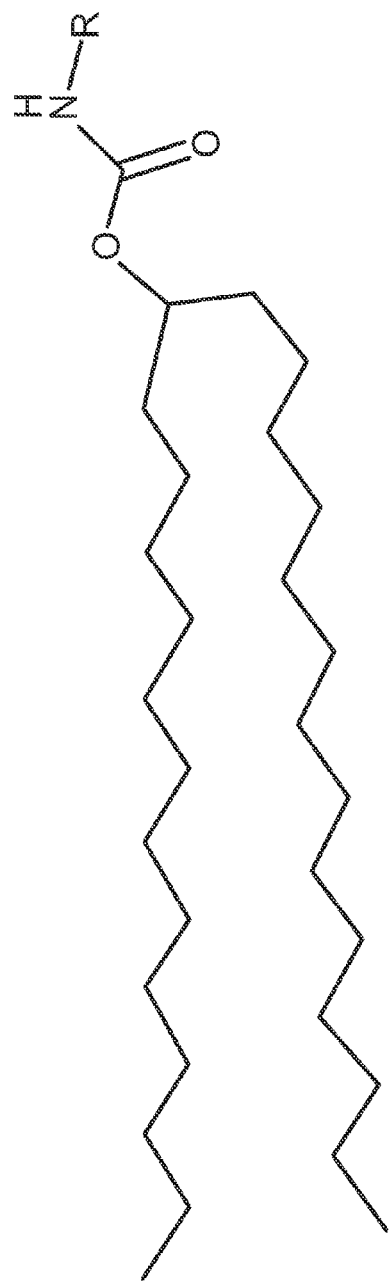
FIGS. 18A to 18E show structures of various PEG-conjugated lipids, where R is PEG of a desired length.
Figure 18B:
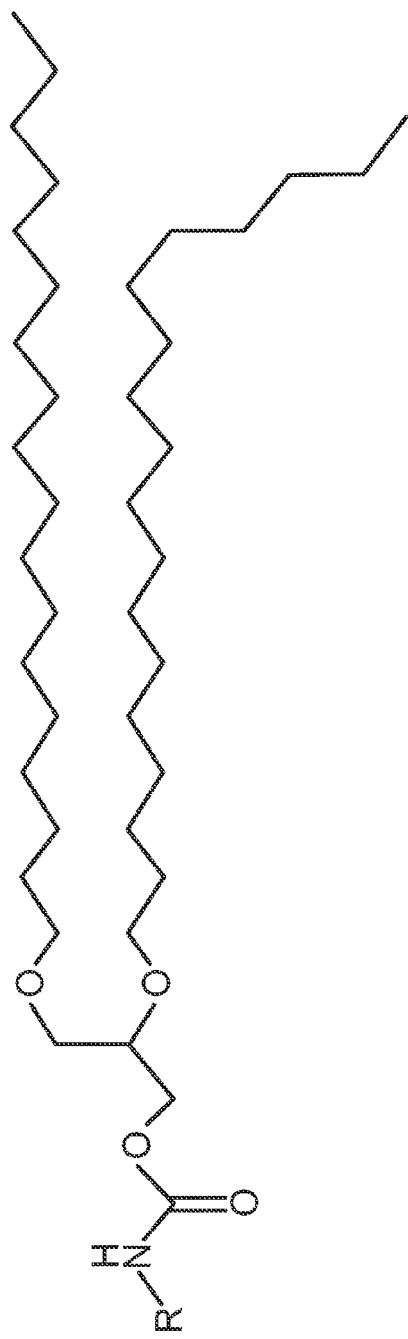
Figure 18C:
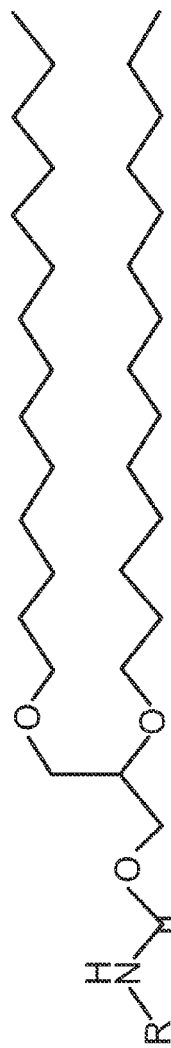
Figure 18D:
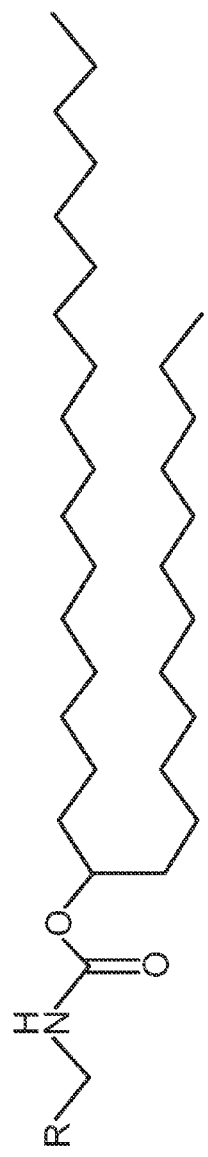
Figure 18E:
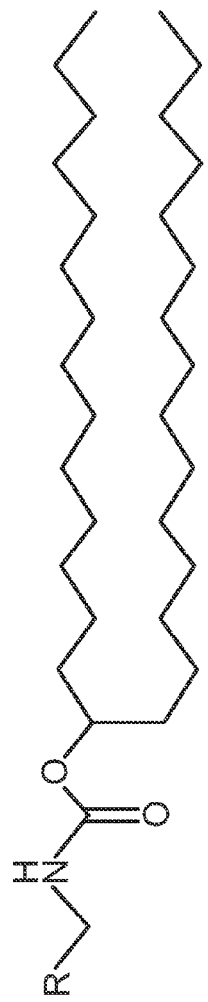

Physical characteristics of the liposomes, made by method (H), were:

| Name | PEGylated lipid | PEG length | Zav (nm) | pdI | % encapsulat[n] |
|---|---|---|---|---|---|
| A | DMG | 2000 | 136.3 | 0.087 | 85.35 |
| B | DMG | 3000 | 120.9 | 0.087 | 72.06 |
| C | DMG | 1000 | 175.9 | 0.111 | 92.52 |
| D | FIG. 18A | 2000 | 157.9 | 0.094 | 97.44 |
| E | FIG. 18D | 2000 | 122.2 | 0.122 | 77.84 |
| F | FIG. 18E | 2000 | 129.8 | 0.125 | 82.57 |
| G | Cholesterol | 2000 | 122.9 | 0.087 | 87.1 |
| H | FIG. 18C | 2000 | 138 | 0.137 | 78.48 |
| I | FIG. 18B | 2000 | 113.4 | 0.091 | 89.12 |

BALB/c mice, 8 per group, were given bilateral intramuscular vaccinations (50 μL per leg) on days 0 and 21 with the replicon, either naked (1 μg) or encapsulated (0.1 μg). Serum was collected for antibody analysis on days 14, and 35.

F-specific serum IgG titers (GMT) were as follows, 2 weeks after the two injections (2wp1):

| RV | 2wp1 | 2wp2 |
|---|---|---|
| Naked RNA | 216 | 1356 |
| A | 3271 | 15659 |
| B | 3860 | 22378 |
| C | 1691 | 7412 |
| D | 1025 | 1767 |
| E | 1618 | 9536 |
| F | 2684 | 11221 |
| G | 3514 | 10566 |
| H | 4142 | 22810 |
| I | 952 | 10410 |

The results show a trend, indicating that higher molecular weight PEG head groups are more immunogenic. As the length of DMG-conjugated PEG increases from 1000 Da to 3000 Da the 2wp2 F-specific IgG titers increase from 7412 to 15659 to 22378.

Changing the linker region from ester to ether did not impact the titers substantially. Also, at the same molecular weight of the head group (2000) there was a trend that increasing the length of the lipid tails lowers the titers (H with C14 dialkyl vs. I with C18 dialkyl). Replacing a PEG di-alkyl lipid tail with cholesterol had little impact on immunogenicity (A with DMG vs. G with cholesterol).

Similar experiments were performed with different lipids in which the 2 kDa of PEG is split into 2×1 kDa groups (FIG. 17). The vA317 replicon was again used, with BALB/c mice, 8 per group, given bilateral intramuscular vaccinations (50 μL per leg) on days 0 & 21 with 1 μg naked RNA or 0.1 μg liposome-encapsulated RNA. The liposomes all had 40% cationic lipid (DlinDMA), 10% DSPC and 48% cholesterol, but the remaining 2% was varied, with different PEGylated lipids (but all with 2 kDa PEG). They were made by method (H).

Physical characteristics of the liposomes were:

| Name | PEGylated lipid | Zav (nm) | pdI | % encapsul$^n$ |
|---|---|---|---|---|
| A | DMG | 121 | 0.101 | 84.84 |
| B | Split; R = C14 saturated | 141.3 | 0.049 | 95.41 |
| C | Split; R = C16 saturated | 114.6 | 0.101 | 96.79 |
| D | Split; R = C18 saturated | 116.5 | 0.088 | 98.63 |
| E | Split; R = C18, 1 unsaturated | 129.4 | 0.149 | 93.37 |

Further liposomes were made with RV05. The liposomes all had 40% cationic lipid (RV05) and 2% PEGylated lipid (2 kDa PEG), but the remaining components varied (although cholesterol was always included). The liposomes were made by method (H) but with pH 5. Physical characteristics were:

| Name | PEGylated lipid | Other components | Zav (nm) | pdI | % encapsul$^n$ |
|---|---|---|---|---|---|
| F | DMG | 10% DSPC, 48% chol | 102.2 | 0.12 | 76.81 |
| G | Cholesterol | 10% DSPC, 46% chol, 2% αGC | 103.7 | 0.107 | 72.58 |
| H | DMG | 10% DPyPE, 48% chol | 99.6 | 0.115 | 78.34 |
| I | DMG | 10% 18:3 PC, 48% chol | 130 | 0.14 | 87.92 |
| J | DMG | 10% 18:2 PC, 48% chol | 101.1 | 0.133 | 76.64 |
| K | DMG | 30% 18:2 PC, 28% chol | 134.3 | 0.158 | 57.76 |

αGC = α-galactosylceramide

BALB/c mice, 8 per group, were given bilateral intramuscular vaccinations (50 μL per leg) on days 0 and 21 with the replicon, either naked (1 μg) or encapsulated (0.1 μg). Serum was collected for antibody analysis on days 14, and 35. F-specific serum IgG titers (GMT) were as follows, 2 weeks after the two injections (2wp1):

| RV | 2wp1 | 2wp2 |
|---|---|---|
| Naked RNA | 321 | 915 |
| A | 2761 | 17040 |
| B | 866 | 3657 |
| C | 1734 | 5209 |
| D | 426 | 2079 |
| E | 2696 | 15794 |
| F | 551 | 955 |
| G | 342 | 2531 |
| H | 1127 | 3881 |
| I | 364 | 1741 |
| J | 567 | 5679 |
| K | 1251 | 5303 |

Splitting the PEG head groups thus lowered in vivo titers. Including a double bond (1 degree of instauration per alkyl tail) in the PEG lipid tails increased IgG titers, 6 fold at day 14 and 7 fold at day 35. For a cationic lipid with an asymmetrical lipid tails (alkyl+cholesterol), changing the neutral lipid from DSPC (saturated C18 lipid tail) to 18:2 or 18:3 PC (with 2 and 3 unsaturated double bonds per tail) increased total IgG titers. Comparable results were observed with replacement of DSPC with DPyPE.

CMV Immunogenicity

RV01 liposomes with DLinDMA as the cationic lipid were used to deliver RNA replicons encoding cytomegalovirus (CMV) glycoproteins. The "vA160" replicon encodes full-length glycoproteins H and L (gH/gL), whereas the "vA322" replicon encodes a soluble form (gHsol/gL). The two proteins are under the control of separate subgenomic promoters in a single replicon; co-administration of two separate vectors, one encoding gH and one encoding gL, did not give good results.

BALB/c mice, 10 per group, were given bilateral intramuscular vaccinations (50 μL per leg) on days 0, 21 and 42 with VRPs expressing gH/gL (1×10$^6$ IU), VRPs expressing gHsol/gL (1×10$^6$ IU) and PBS as the controls. Two test groups received 1 μg of the vA160 or vA322 replicon formulated in liposomes (40% DlinDMA, 10% DSPC, 48% Chol, 2% PEG-DMG; made using method (D) but with 150 μg RNA batch size).

The vA160 liposomes had a Zav diameter of 168.8 nm, a pdI of 0.144, and 87.4% encapsulation. The vA322 liposomes had a Zav diameter of 162 nm, a pdI of 0.131, and 90% encapsulation.

The replicons were able to express two proteins from a single vector.

Sera were collected for immunological analysis on day 63 (3wp3). CMV neutralization titers (the reciprocal of the serum dilution producing a 50% reduction in number of positive virus foci per well, relative to controls) were as follows:

| gH/gL VRP | gHsol/gL VRP | gH/gL liposome | gHsol/gL liposome |
|---|---|---|---|
| 4576 | 2393 | 4240 | 10062 |

RNA expressing either a full-length or a soluble form of the CMV gH/gL complex thus elicited high titers of neutralizing antibodies, as assayed on epithelial cells. The average titers elicited by the liposome-encapsulated RNAs were at least as high as for the corresponding VRPs.

Repeat experiments confirmed that the replicon was able to express two proteins from a single vector. The RNA replicon gave a 3wp3 titer of 11457, compared to 5516 with VRPs.

It will be understood that the invention has been described by way of example only and modifications may be made whilst remaining within the scope and spirit of the invention.

TABLE 1

| | useful phospholipids |
|---|---|
| DDPC | 1,2-Didecanoyl-sn-Glycero-3-phosphatidylcholine |
| DEPA | 1,2-Dierucoyl-sn-Glycero-3-Phosphate |
| DEPC | 1,2-Erucoyl-sn-Glycero-3-phosphatidylcholine |
| DEPE | 1,2-Dierucoyl-sn-Glycero-3-phosphatidylethanolamine |
| DEPG | 1,2-Dierucoyl-sn-Glycero-3[Phosphatidyl-rac-(1-glycerol . . . ) |
| DLOPC | 1,2-Linoleoyl-sn-Glycero-3-phosphatidylcholine |
| DLPA | 1,2-Dilauroyl-sn-Glycero-3-Phosphate |
| DLPC | 1,2-Dilauroyl-sn-Glycero-3-phosphatidylcholine |
| DLPE | 1,2-Dilauroyl-sn-Glycero-3-phosphatidylethanolamine |
| DLPG | 1,2-Dilauroyl-sn-Glycero-3[Phosphatidyl-rac-(1-glycerol . . . ) |
| DLPS | 1,2-Dilauroyl-sn-Glycero-3-phosphatidylserine |
| DMG | 1,2-Dimyristoyl-sn-glycero-3-phosphoethanolamine |
| DMPA | 1,2-Dimyristoyl-sn-Glycero-3-Phosphate |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG | 1,2-Myristoyl-sn-Glycero-3[Phosphatidyl-rac-(1-glycerol . . . ) |
| DMPS | 1,2-Dimyristoyl-sn-Glycero-3-phosphatidylserine |
| DOPA | 1,2-Dioleoyl-sn-Glycero-3-Phosphate |

TABLE 1-continued useful phospholipids

| | |
|---|---|
| DOPC | 1,2-Dioleoyl-sn-Glycero-3-phosphatidylcholine |
| DOPE | 1,2-Dioleoyl-sn-Glycero-3-phosphatidylethanolamine |
| DOPG | 1,2-Dioleoyl-sn-Glycero-3[Phosphatidyl-rac-(1-glycerol...) |
| DOPS | 1,2-Dioleoyl-sn-Glycero-3-phosphatidylserine |
| DPPA | 1,2-Dipalmitoyl-sn-Glycero-3-Phosphate |
| DPPC | 1,2-Dipalmitoyl-sn-Glycero-3-phosphatidylcholine |
| DPPE | 1,2-Dipalmitoyl-sn-Glycero-3-phosphatidylethanolamine |
| DPPG | 1,2-Dipalmitoyl-sn-Glycero-3[Phosphatidyl-rac-(1-glycerol...) |
| DPPS | 1,2-Dipalmitoyl-sn-Glycero-3-phosphatidylserine |
| DPyPE | 1,2-diphytanoyl-sn-glycero-3-phosphoethanolamine |
| DSPA | 1,2-Distearoyl-sn-Glycero-3-Phosphate |
| DSPC | 1,2-Distearoyl-sn-Glycero-3-phosphatidylcholine |
| DSPE | 1,2-Diostearpyl-sn-Glycero-3-phosphatidylethanolamine |
| DSPG | 1,2-Distearoyl-sn-Glycero-3[Phosphatidyl-rac-(1-glycerol...) |
| DSPS | 1,2-Distearoyl-sn-Glycero-3-phosphatidylserine |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl-2-oleoyl-sn-Glycero-3-phosphatidylethanolamine |
| POPG | 1,2-Dioleoyl-sn-Glycero-3[Phosphatidyl-rac-(1-glycerol)...] |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

REFERENCES

[1] Johanning et al. (1995) *Nucleic Acids Res* 23:1495-1501.
[2] Heyes et al. (2005) *J Controlled Release* 107:276-87.
[3] WO2005/121348.
[4] *Liposomes: Methods and Protocols, Volume 1: Pharmaceutical Nanocarriers: Methods and Protocols.* (ed. Weissig). Humana Press, 2009. ISBN 160327359X.
[5] *Liposome Technology*, volumes I, II & III. (ed. Gregoriadis). Informa Healthcare, 2006.
[6] *Functional Polymer Colloids and Microparticles volume 4 (Microspheres, microcapsules & liposomes).* (eds. Arshady & Guyot). Citus Books, 2002.
[7] Jeffs et al. (2005) *Pharmaceutical Research* 22 (3):362-372.
[8] WO2005/113782.
[9] WO2011/005799.
[10] El Ouahabi et al. (1996) *FEBS Letts* 380:108-12.
[11] Giuliani et al. (2006) *Proc Natl Acad Sci USA* 103(29): 10834-9.
[12] WO2009/016515.
[13] WO02/34771.
[14] WO2005/032582.
[15] WO2010/119343.
[16] WO2006/110413.
[17] WO2005/111066.
[18] WO2005/002619.
[19] WO2006/138004.
[20] WO2009/109860.
[21] WO02/02606.
[22] WO03/018054.
[23] WO2006/091517.
[24] WO2008/020330.
[25] WO2006/089264.
[26] WO2009/104092.
[27] WO2009/031043.
[28] WO2007/049155.
[29] Gennaro (2000) *Remington: The Science and Practice of Pharmacy.* 20th edition, ISBN: 0683306472.
[30] *Methods In Enzymology* (S. Colowick and N. Kaplan, eds., Academic Press, Inc.)
[31] *Handbook of Experimental Immunology*, Vols. I-IV (D. M. Weir and C. C. Blackwell, eds, 1986, Blackwell Scientific Publications)
[32] Sambrook et al. (2001) *Molecular Cloning: A Laboratory Manual,* 3rd edition (Cold Spring Harbor Laboratory Press).
[33] *Handbook of Surface and Colloidal Chemistry* (Birdi, K. S. ed., CRC Press, 1997)
[34] Ausubel et al. (eds) (2002) *Short protocols in molecular biology,* 5th edition (Current Protocols).
[35] *Molecular Biology Techniques: an intensive laboratory course* (Ream, eds. 1998 Academic Press)
[36] *PCR (Introduction to Biotechniques Series),* 2nd ed. (Newton & Graham eds. 1997, Springer Verlag)
[37] Yoneyama & Fujita (2007) *Cytokine & Growth Factor Reviews* 18:545-51.
[38] Maurer et al. (2001) *Biophysical Journal,* 80: 2310-2326.
[39] Perri et al. (2003) *J Virol* 77:10394-10403.
[40] Boxus et al. (2007) *J Virol* 81:6879-89.
[41] Taylor et al. (2005) *Vaccine* 23:1242-50.
[42] WO2011/076807.
[43] WO2011/057020.

The invention claimed is:

1. A pharmaceutical composition comprising a population of liposomes and a population of immunogen-encoding RNA molecules,
wherein the average diameter of the liposomes in the population is about 100 nm, with a polydispersity index of less than about 0.1, wherein said population of liposomes comprise: (i) 20%-80% (molar percent) cationic lipid or lipids; (ii) a zwitterionic lipid; and (iii) 20%-80% (molar percent) cholesterol; wherein at least half of the population of RNA molecules are encapsulated in liposomes, wherein said population of RNA molecules are self-replicating RNA molecules that encode (a) a RNA-dependent RNA polymerase which can transcribe RNA from the self-replicating RNA and (b) an immunogen, and wherein said population of RNA molecules are not packaged in virion particles.

2. The liposome of claim 1, wherein the RNA is 5000-25000 nucleotides long.

3. The liposome of claim 1, wherein the self-replicating RNA is a (+)-stranded RNA.

4. The liposome of claim 1, wherein the self-replicating RNA has two open reading frames, the first of which encodes an alphavirus replicase and the second of which encodes the immunogen.

5. The liposome of claim 2, wherein the self-replicating RNA is 9000-12000 nucleotides long.

6. The liposome of claim 1, wherein the immunogen can elicit an immune response in vivo against a bacterium, a virus, a fungus or a parasite.

7. A pharmaceutical composition comprising a liposome of claim 1.

8. The pharmaceutical composition of claim 7, wherein said population of liposomes comprise 35%-50% (molar percent) cholesterol.

9. The liposome of claim 1, wherein said liposome comprises DlinDMA (1,2-dilinoleyloxy-N,N-dimethyl-3-aminopropane), DSPC (1,2-Diastearoyl-sn-glycero-3-phosphocholine), DPyPE (1,2-diphytanoyl-sn-glycero-3-phosphoethanolamine), a cholesterol, a PEGylated lipid, or a combination thereof.

10. The pharmaceutical composition of claim 1, wherein said population of liposomes comprise 35%-50% (molar percent) cholesterol.

11. The pharmaceutical composition of claim 1, wherein said population of liposomes comprise 30%-70% (molar percent) cationic lipid or lipids.

12. A method for raising a protective immune response in a vertebrate, comprising the step of administering to the vertebrate an effective amount of the pharmaceutical composition of claim 1.

* * * * *